US005736325A

United States Patent [19]

Manowitz et al.

[11] Patent Number: 5,736,325
[45] Date of Patent: Apr. 7, 1998

[54] MARKER FOR INDIVIDUALS SUSCEPTIBLE TO ALCOHOLISM

[75] Inventors: Paul Manowitz, East Brunswick; Ronald D. Poretz, Marlboro, both of N.J.; David Park, New York, N.Y.; Michael Ricketts, Somerset, N.J.

[73] Assignee: Algene LLC, East Brunswick, N.J.

[21] Appl. No.: 299,187

[22] Filed: Aug. 31, 1994

[51] Int. Cl.$^6$ .................. C12Q 1/68; G01N 33/573; C07H 21/04; C12N 15/00
[52] U.S. Cl. ................ 435/6; 435/7.1; 435/7.4; 435/91.1; 435/91.2; 435/810; 435/975; 435/183; 530/387.1; 530/388.1; 530/388.26; 530/388.85; 536/23.1; 536/23.5; 536/24.31; 536/24.33; 536/25.3; 935/76; 935/77; 935/78
[58] Field of Search .................. 435/6, 91.1, 91.2, 435/183, 810, 7.1, 7.4, 975; 436/94, 513; 536/23.1, 23.5, 24.31, 24.33, 25.3; 935/76–78; 530/387.1, 388.1, 388.26, 388.85

[56] References Cited

U.S. PATENT DOCUMENTS

| | | | |
|---|---|---|---|
| 4,800,159 | 1/1989 | Mullis et al. | 435/172.3 |
| 4,918,102 | 4/1990 | Dobbins . | |
| 5,013,752 | 5/1991 | Dobbins . | |
| 5,162,203 | 11/1992 | Vallee . | |
| 5,210,016 | 5/1993 | Blum et al. . | |
| 5,464,742 | 11/1995 | Swift et al. | 435/6 |

OTHER PUBLICATIONS

Park, D., et al., "Human Fibroblast Arylsulfatase A: Structure, Metabolism, and Cellular Localization of Variant Forms," Abstract No. 744, The Faseb Journal, vol. 7, No. 7, A1180, Apr. 20, 1993.
Nelson, P.V., et al., "Population frequency of the arylsulphatase A pseudogo–deficiency allele," H/uman Genetics, vol. 87, pp. 87–88, 1991.
Hulyalkar, A. R., et al., "Arylsulfatase A Variants in patients with Alcoholism," Alcoholism : Clinical and Experimental Research, vol. 8, No. 3, pp. 337–341, May 1984.
Oellerich, M. (1984) J. Clin. Chem. Clin. Biochem. 22:895–904.
Chabás et al., 1993, Clin. Genet. 44:320–323.
Park et al., 1993, FASEB J. 7:A1180 (abstract #744).
Penzien et al., 1993, Am. J. Hum. Genet. 52:557–64.
Shen et al., 1993, Am. J. Med. Genet., 45:631–637.
Poretz et al., 1992, Biochem. J. 287:979–983.
Gieselmann V., 1991, Hum. Genet. 86:251–55.
Gieselmann et al., 1991, Dev. Neurosci., 13:222–27.
Kappler et al., 1991, Hum. Genet. 86:463–470.
Nelson et al., 1991, Hum. Genet. 87:87–88.
Wenger and Louie, 1991, Dev. Neurosci. 13:216–221.
Ameen et al., 1990, Mol. Cell. Biochem. 92:117–127.
Gieselmann et al., 1989, Proc. Natl. Acad. Sci. USA 86:9436–9440.
Hohenschutz et al., 1989, Hum. Genet. 82:45–8.
Kolodny, 1989, *Metabolic Basis fo Inherited Disease*, vol. II, C.R. Scriver et al. (Eds.), McGraw-Hill: New York, pp. 1721, 1730, 1737–1740.
Stein et al., 1989, J. Biol. Chem. 264:1252–1259.
Hohenschutz et al., 1988, Am. J. Med. Genet. 31:169–75.
Ameen and Chang, 1987, FEBS Lett. 219:130–134.
Wu et al., 1986, J. Biol. Chem. 261:3687–3691.
Hulyalkar et al., 1984, Alcoh. Clin. Exp. Res. 8:337–341.
Manowitz et al., 1981, Biol. Psychiatry 16:1107–13.
Craves et al., 1980, Science 207:75–76.
Rawat, A.K., 1974, Res. Commun. Chem. Pathol. Pharm. 8:461–469.

*Primary Examiner*—Bradley L. Sisson
*Attorney, Agent, or Firm*—Klauber & Jackson

[57] ABSTRACT

The present invention relates to methods for diagnosis of susceptibility to alcoholism or the pathological effects of alcoholism based on detection of a genetic marker in an individual. The present invention is directed generally to methods and associated compositions and kits for detecting the presence of arylsulfatase A (ASA) pseudodeficiency (PD) mutations in humans. Detection of these mutations has been surprisingly found to be a strong indicator for susceptibility to alcoholism and/or susceptibility to alcohol's pathological effects, as well as an important marker in evaluating the likelihood of metachromatic leukodystrophy (MLD).

44 Claims, 2 Drawing Sheets

FIG.1A
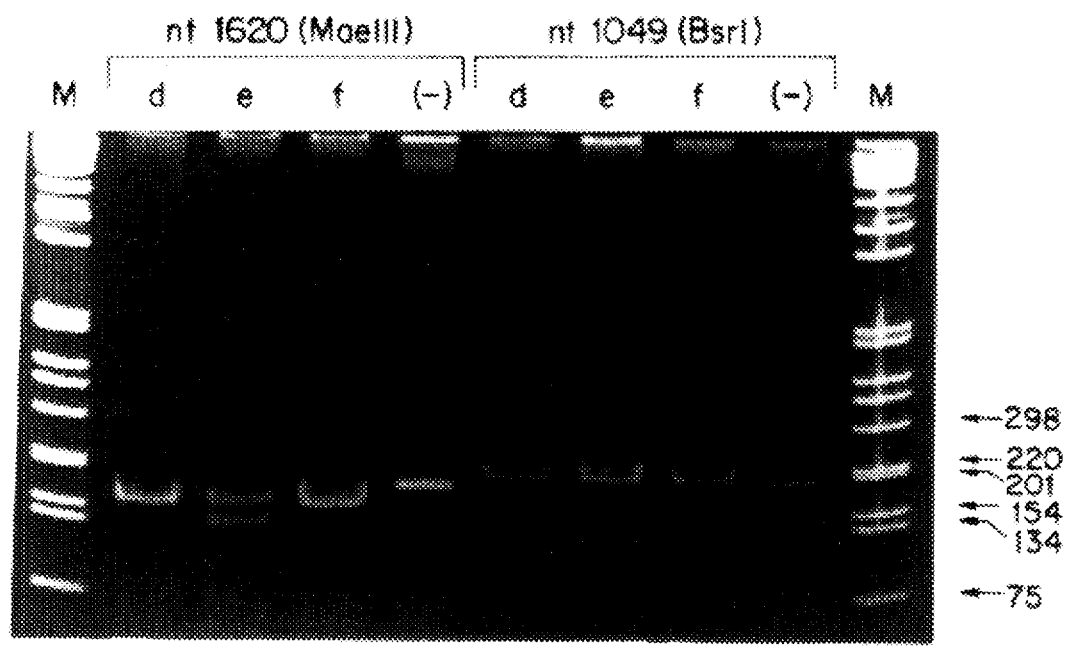
FIG.1B
|  | SUBJECTS | | | | | |
|---|---|---|---|---|---|---|
|  | a | b | c | d | e | f |
| PolyA signal site | -/- | +/+ | +/- | -/- | +/- | -/- |
| N-glycosylation site | -/- | +/+ | +/- | -/- | +/- | +/- |
FIG.1C

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo sapiens ( x ) PUBLICATION INFORMATION:
  ( A ) AUTHORS: Gieselmann, Volkmar
      Polten, Andreas
      Kreysing, Joachim
      von Figura, Kurt
  ( B ) TITLE: Arylsulfatase A pseudodeficiency: Loss of a polyadenylation signal and N-glycosylation site
  ( C ) JOURNAL: Proc. Natl. Acad. Sci. U.S.A.
  ( D ) VOLUME: 86
  ( F ) PAGES: 9436-9440
  ( G ) DATE: December-1989

( x i ) SEQUENCE DESCRIPTION: SEQ ID NO:1:

TTGATGGCGA ACTGAGTGAC 20

( 2 ) INFORMATION FOR SEQ ID NO:2:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION:SEQ ID NO:2:

CGAAGCACTG CACATACCTG G    2

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION:SEQ ID NO:3:

GCTCTATGAC CTGTCCAAGG ACC    2

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (x) PUBLICATION INFORMATION:
        (A) AUTHORS: Gieselmann, Volkmar
                Polten, Andreas
                Kreysing, Joachim
                von Figura, Kurt
        (B) TITLE: Arylsulfatase A pseudodeficiency: Loss of a
            polyadenylation signal and N-glycosylation site
        (C) JOURNAL: Proc. Natl. Acad. Sci. U.S.A.
        (D) VOLUME: 86
        (F) PAGES: 9436-9440
        (G) DATE: December-1989

(xi) SEQUENCE DESCRIPTION: SEQ ID NO:4:

TTCCTCATTC GTACCACAGG    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (x) PUBLICATION INFORMATION:
        (A) AUTHORS: Gieselmann, Volkmar
                Polten, Andreas
                Kreysing, Joachim von Figura, Kurt
   ( B ) TITLE: Arylsulfatase A pseudodeficiency: Loss of a
         polyadenylation signal and N-glycosylation site
   ( C ) JOURNAL: Proc. Natl. Acad. Sci. U.S.A.
   ( D ) VOLUME: 86
   ( F ) PAGES: 9436-9440
   ( G ) DATE: December-1989

( x i ) SEQUENCE DESCRIPTION: SEQ ID NO:5:

AAGGTGACAT TGGGCAGTGG                                                                        20

( 2 ) INFORMATION FOR SEQ ID NO:6:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
         ( A ) ORGANISM: Homo sapiens ( x ) PUBLICATION INFORMATION:
         ( A ) AUTHORS: Gieselmann, Volkmar
                  Polten, Andreas
                  Kreysing, Joachim
                  von Figura, Kurt
         ( B ) TITLE: Arylsulfatase A pseudodeficiency: Loss of a
                  polyadenylation signal and N-glycosylation site
         ( C ) JOURNAL: Proc. Natl. Acad. Sci. U.S.A.
         ( D ) VOLUME: 86
         ( F ) PAGES: 9436-9440
         ( G ) DATE: December-1989

( x i ) SEQUENCE DESCRIPTION: SEQ ID NO:6:

AAGGTGACAC TGGGCAGTGG                                                                        20

( 2 ) INFORMATION FOR SEQ ID NO:7:

( i ) SEQUENCE CHARACTERISTICS:
         ( A ) LENGTH: 19 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
         ( A ) ORGANISM: Homo sapiens ( x ) PUBLICATION INFORMATION:
         ( A ) AUTHORS: Gieselmann, Volkmar
                  Polten, Andreas
                  Kreysing, Joachim
                  von Figura, Kurt
         ( B ) TITLE: Arylsulfatase A pseudodeficiency: Loss of a
                  polyadenylation signal and N-glycosylation site
         ( C ) JOURNAL: Proc. Natl. Acad. Sci. U.S.A.
         ( D ) VOLUME: 86
         ( F ) PAGES: 9436-9440
         ( G ) DATE: December-1989

( x i ) SEQUENCE DESCRIPTION: SEQ ID NO:7:

CTGGTGTTAT TACGTTATC                                                                         19

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x ) PUBLICATION INFORMATION:
        ( A ) AUTHORS: Gieselmann, Volkmar
            Polten, Andreas
            Kreysing, Joachim
            von Figura, Kurt
        ( B ) TITLE: Arylsulfatase A pseudodeficiency: Loss of a
            polyadenylation signal and N-glycosylation site
        ( C ) JOURNAL: Proc. Natl. Acad. Sci. U.S.A.
        ( D ) VOLUME: 86
        ( F ) PAGES: 9436-9440
        ( G ) DATE: December-1989

( x i ) SEQUENCE DESCRIPTION: SEQ ID NO:8:

```
CTGGTGTTAC TACGTTATC                                                        19
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:9:

```
TGATGGCGAA CTGAGTGACT                                                       20
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:10:

```
AAGGATCTGG GATCAGGGGT                                                       20
```

( 2 ) INFORMATION FOR SEQ ID NO:11:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:11:

AGCTTGCTGC CATTGCCCA                                                                    19

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:12:

CATTACCCCA GGATTGGTCG AA                                                     22

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens
        ( C ) INDIVIDUAL ISOLATE: peptide from mutant arylsulfatase A ( x i ) SEQUENCE DESCRIPTION: SEQ ID NO:13:

Cys Ala Pro Leu Pro Ser Val Thr Leu Asp Gly Phe Asp
1                5                            10

MARKER FOR INDIVIDUALS SUSCEPTIBLE TO ALCOHOLISM

The research leading to the present invention was supported in part with funds from National Institute on Alcoholism and Alcohol Abuse Grant No. ROI-AA-07799. The Government may have certain rights in the invention.

FIELD OF THE INVENTION

The present invention relates to methods for diagnosis of susceptibility to alcoholism or the pathological effects of alcoholism based on detection of a genetic marker in an individual.

BACKGROUND OF THE INVENTION

A large number of adoption and twin studies indicate that there is a genetic factor or factors to at least some forms of alcoholism (Goodwin, 1979, Arch. Gen. Psychiatry 36:57–61). However, to date, the only genetic factor that has been clearly identified in alcoholism is a deficiency in aldehyde dehydrogenase activity. This deficiency leads to a reduction, not an increase, in the rate of alcoholism.

Earlier studies showed that arylsulfatase A (ASA) electrophoresed in native polyacrylamide gels and stained for enzymatic activity exhibited a variety of electrophoretic patterns, some of which were more likely to be found in alcoholic patients than in non-alcoholic psychiatric and normal control subjects (Hulyalkar et al., 1984, Alcoh.: Clin. Exp. Res. 8:337–341). However, lacking any biochemical explanation for these observations, no correlation with a genetic basis or marker for alcoholism was possible.

A more severe neuropathological disease associated with a deficiency of ASA is metachromatic leukodystrophy (MLD). MLD is a debilitating genetic disease characterized by neuropsychological deficits. In late-onset MLD, the initial symptoms include attentional difficulties, hyperactivity, impulsivity, poor judgement, and emotional lability (Shapiro et al., 1994, Neurology 44:662–665).

MLD patients display a characteristic demyelination pathology resulting from increased levels of sulfatides. This glycolipid comprises a significant proportion of the myelin sheath and accumulates in oligodendrocytes and Schwann cells of individuals with MLD.

MLD is caused by the lack of the enzyme activity of arylsulfatase A (ASA, EC 3.1.6.8), a lysosomal glycoprotein which catalyzes the desulfation of sulfatides, the first step in sulfatide catabolism.

Some individuals exhibit much reduced levels of ASA activity, but appear to catabolize sulfatides adequately and lack apparent MLD-related neurological symptoms (Kolodny, E. H., 1989, The Metabolic Basis of Inherited Disease, eds., pp. 1721–1750). These people are pseudodeficient for ASA (PD-ASA) and possess an ASA gene which has two A-G transitions. One of these mutations results in an $Asn_{350}$ to Ser conversion, causing a loss of a potential N-glycosylation site, and the other in a polyadenylation signal consensus sequence alteration, resulting in a reduction of a 2.1 Kb message (Gieselmann et al., 1989, Proc. Natl. Acad. Sci. U.S.A. 86:9436–9440). The PD-ASA gene frequency, at approximately 10%, is quite common (Nelson et al., 1991, Hum. Genet. 87:87–88). A number of multiband electrophoretic variants of ASA are found in the general population (Poretz, et al., 1992, Biochem. J. 287:979–983). Some of the inventors herein have previously demonstrated flint the electrophoretic (non-denaturing) pattern is due to a heterogeneous mixture of ASA isoforms with variable degrees of phosphorylation of the N-glycan moieties, and hypothesized that the variant forms may reflect differences in both the structure of the carbohydrate units and polypeptide of the enzyme ((Poretz, et al., 1992, Biochem. J. 287:979–983; Park et al., 1993, FASEB J. 7:744 (abstract)).

The pseudodeficiency mutations do not cause MLD but reduce the enzyme activity of ASA sufficiently to complicate the diagnosis of MLD and MLD carrier status in families where they occur (Gieselmann et al., 1991, Dev Neurosci. 86:9436–9440; Wenger & Louie, 1991, Dev. Neurosci., 13:216–221). While the polyadenylation signal sequence mutation has been proposed to be the cause of the reduced ASA activity in pseudodeficiency (Gieselmann et al., 1989, Proc. Natl. Acad. Sci. U.S.A., 86:9436–9440) there is evidence that the N-glycosylation site mutation also reduces ASA enzyme activity (Shen et al., 1993, Am. J. Med. Genet., 45:631–637). This is significant as the N-glycosylation site mutation can occur in the absence of the polyadenylation signal site mutation (Nelson et al., 1991, Hum. Genet., 87:87–88; Shen et al., 1993, Am. J. Med. Genet., 45:631–637). The ability to distinguish this mutation is therefore important in diagnosis and risk determination in families with MLD (Shen et al., 1993, Am. J. Med. Genet., 45:631–637).

Previously, allele specific tests have been described (Gieselmann et al., 1989, Proc. Natl. Acad. Sci. U.S.A. 86:9436; Gieselmann et al., 1991, Human Gen. 86:251). However, no clear relationship between neurologic disease and enzyme deficiency has been conclusively established (Kolodny, 1989, in *Metabolic Basis of herited Disease*, Vol. II, C. R. Scriber et al. (Eds.), McGraw-Hill: New York, pp. 1721–1740). In particular, homozygosity for the ASA-PD allele has been reported to bear no clinical consequence, and that homozygosity for the ASA-PD allele is no more frequent among neuropsychiatric patients than normal controls (Hohenschutz et al., 1988, Am. J. Med. Genet. 31:169–175). Individuals who present with an $ASA^{negative}$/ASA-PD genotype (i.e., heterozygous MLD) may have a greater incidence of clinical abnormalities (hohenschutz et al., 1989, Human Genet. 82:45–48). A more recent publication disputes this hypothesis (Penzien et al., 1993, Am. J. Hum. Genet. 52:557–564).

SUMMARY OF THE INVENTION

The present invention is directed generally to methods and associated compositions and kits for detecting the presence of arylsulfatase A (ASA) pseudodeficiency (PD) mutations in humans. Detection of these mutations has been surprisingly found to be a strong indicator for susceptibility to alcoholism and/or susceptibility to alcohol's pathological effects, as well as an important marker in evaluating the likelihood of metachromatic leukodystrophy (MLD).

Accordingly, in a first aspect, the invention is directed to a method for identifying an individual who may be susceptible to alcoholism or to the pathological effects of alcohol comprising identifying an whether individual is homozygous, heterozygous, or normal for a pseudodeficiency (PD) mutation in the arylsulfatase A (ASA) gene, wherein homozygosity for a PD mutation in each allele of the ASA gene indicates that the individual may be susceptible to alcoholism. In particular, the invention relates to detecting a mutation in a residue 350 N-glycosylation site of ASA, or to detecting a mutation in a polyadenylation signal sequence of at least one allele of ASA, or to detecting both mutations in an ASA allele.

The methods of the invention are advantageously carried out using polymerase chain amplification (PCR) analysis. Preferably, the PCR product of the mutant and normal ASA can be differentiated by specific restriction endonucleases. In a specific embodiment, the PCR analysis for the mutation in the residue 350 N-glycosylation site can be performed by amplifying an approximately 200-base pair segment of genomic DNA with a 5' primer TGATGGCGAACTGAGT-GACT (SEQ ID NO:9) and a 3' primer AAGGATCTGG-GATCAGGGGT (SEQ ID NO:10); and detecting the presence of a BsrI restriction endonuclease site; wherein the BsrI endonuclease site is present in the PD mutant ASA allele. In another specific embodiment, the analysis for the mutation in the polyadenylation signal sequence can be performed by amplifying about an approximately 182-base pair segment of genomic DNA with a 5' primer AGCTTGCTGCCAT-TGCCCA (SEQ ID NO:11) and a 3' primer CATTAC-CCCAGGATTGGTCGAA (SEQ ID NO:12); and detecting the presence of two MaeIII restriction endonuclease sites; wherein two MaeIII endonuclease sites are present in the PD mutant ASA allele.

Alternatively, the PCR product can be probed with probes specific for the wild type (normal) and mutated sequences of ASA gene. In a specific embodiment, a segment of genomic DNA or mRNA containing the N-glycosylation site is amplified by PCR, and analyzed by hybridization of an oligonucleotide probe selected from the group consisting of AAGGTGACATTGGGCAGTGG (SEQ ID NO:5) and AAGGTGACACTGGGCAGTGG (SEQ ID NO:6) to the amplified sequence, wherein hybridization of the former probe at 55° C. with washing at 62° C. is indicative of a normal ASA allele, and hybridization of the latter probe at 55° C. with washing at 60° C. is indicative of a PD allele. In another specific embodiment, a segment of genomic DNA containing the polyadenylation signal site is amplified by PCR, and analyzed by hybridization of an oligonucleotide probe selected from the group consisting of CTGGTGT-TATTACGTTATC (SEQ ID NO:7) and CTGGTGTTAC-TACGTTATC (SEQ ID NO:8) to the amplified sequence, wherein hybridization of the former probe at 48° C. with washing at 52° C. is indicative of a normal ASA allele, and hybridization of the latter probe at 48° C. with washing at 52° C. is indicative of a PD allele.

A particular advantage of the present invention is that the PCR analysis can be performed on DNA obtained from buccal cells. Preferably, the analysis involves identification of restriction endonuclease sites unique to either the mutant ASA or native (wild type) ASA, or both.

The invention further provides for detecting mutant ASA lacking an N-glycan moiety by biochemical analysis. In a specific embodiment, the biochemical analysis comprises detecting a difference in the relative electrophoretic mobility of an ASA protein from an individual possessing the mutant ASA enzyme as compared to a normal ASA protein.

In a preferred aspect, the mutation in the N-glycosylation site is detected by immunochemical analysis. For example, the immunochemical analysis can comprise detecting binding of an antibody specific for an epitope containing residue 350 of ASA lacking an N-glycosylation site, wherein the antibody does not bind to normal ASA. In a preferred embodiment, the antibody is a monoclonal antibody; in a specific Example, preparation of such an antibody against the peptide Ac-CAPLPSVTDGFD-NH$_2$ (SEQ ID NO:13) is described.

To characterize whether an individual is homozygous for the PD alleles of ASA, heterozygous, or homozygous for normal ASA, an antibody assay of the invention contemplates comparing the amount of ASA bound by an antibody specific for the PD mutant ASA to the amount of ASA bound by an antibody that binds to all forms of ASA. If the quantity of ASA bound by the antibody specific for the mutant ASA is about the same as the quantity bound by the antibody reactive with all ASA, then the individual is homozygous for the PD alleles; if the amount of ASA bound by the mutant-specific antibody is about half the amount bound by the antibody reactive with all forms of ASA, then the individual is heterozygous; and if the amount of ASA bound by the mutant-specific antibody is much less than the amount bound by the antibody reactive with all forms of ASA, then the individual is homozygous normal.

Accordingly, the invention relates to an antibody specific for an epitope containing residue 350 of ASA lacking an N-glycosylation site, wherein the antibody does not bind to normal ASA containing the N-glycosylation site. Preferably, the antibody of is a monoclonal antibody, e.g., a murine monoclonal antibody generated against the peptide Ac-CAPLPSVTDGFD-NH$_2$ (SEQ ID NO:13).

The invention further provides kits for identifying an individual who is susceptible to alcoholism or to the pathological effects of alcohol. One such kit comprises the antibody described above, an antibody specific for all forms of ASA; and means for quantitating binding of the antibody specific for an epitope of mutant ASA and the antibody specific for all forms of ASA to ASA in a sample from an individual.

In another embodiment, the invention relates to a method for identifying an individual carrying a pseudodeficiency (PD) mutation of an allele of an arylsulfatase A (ASA) gene, comprising detecting a mutation in a residue 350 N-glycosylation site of at least one allele of ASA by polymerase chain amplification (PCR) analysis, wherein the PCR product of the mutant and normal N-glycosylation site can be differentiated by specific restriction endonucleases. In a further aspect, the invention also relates to a method for identifying an individual carrying a PD mutation of an allele of an ASA gene, comprising detecting a mutation in a polyadenylation signal sequence of at least one allele of ASA by PCR analysis, wherein the PCR product of the mutant and normal polyadenylation signal sequence can be differentiated by specific restriction endonucleases. In a yet another aspect, the a method for identifying an individual carrying a PD mutation of an allele of an ASA gene comprises detecting a mutation in a residue 350 N-glycosylation site of at least one allele of ASA by polymerase chain amplification (PCR) analysis, wherein the PCR product of the mutant and normal N-glycosylation site can be differentiated by specific restriction endonucleases; and detecting a mutation in a polyadenylation signal sequence of at least one allele of ASA by polymerase chain amplification (PCR) analysis, wherein the PCR product of the mutant and normal polyadenylation signal sequence can be differentiated by specific restriction endonucleases. In a preferred embodiment, the specific probes and endonucleases described above are used.

A kit for identifying an individual who is susceptible to alcoholism or to the pathological effects of alcohol, or for evaluating whether the individual has a PD allele of ASA, comprises a 5' primer having the sequence TGATGGC-GAACTGAGTGACT (SEQ ID NO:9) and a 3' primer having the sequence AAGGATCTGGGATCAGGGGT (SEQ ID NO:10) and a BsrI restriction endonuclease; or a 5' primer having the sequence AGCTTGCTGCCATTGCCCA (SEQ ID NO:11) and a 3' primer having the sequence CATTACCCCAGGATTGGTCGAA (SEQ ID NO:12) and a MaeIII restriction endonuclease, or both.

Accordingly, the invention provides an oligonucleotide selected from the group consisting of

TGATGGCGAACTGAGTGACT (SEQ ID NO:9);

AAGGATCTGGGATCAGGGGT (SEQ ID NO:10);

AGCTTGCTGCCATTGCCCA (SEQ ID NO:11);

and

CATTACCCCAGGATTGGTCGAA (SEQ ID NO:12).

Thus, it is an object of the invention to provide convenient methods and reagents for identifying individuals who are carry one or two PD alleles of the ASA gene.

A particular object of the invention is to identify individuals who may have a greater susceptibility to alcoholism, or to the pathological effects of alcohol, or both.

Another object of the invention is to provide methods and reagents to more easily detect the mutations characteristic of the PD alleles of ASA, which can be used for genetic counselling.

These and other objects of the present invention will be made more clear by reference to the following drawings and detailed description of the invention.

BRIEF DESCRIPTION OF THE DRAWINGS

FIGS. 2A–2C. Detection of the pseudodeficiency mutations of ASA. (A) DNA from blood leukocytes of three individuals (a, b and c) was amplified across the polyadenylation site of ASA (nucleotide 1620 of the cDNA) and treated with MaeIII or amplified across the position 350 N-glycosylation site of ASA (position 1049 of the cDNA) and cut with BsrI, as indicated. The lanes indicated (−) represent the amplified DNA product not treated with restriction enzyme. M, DNA size markers, in base pairs (1 kb ladder, Gibco-BRL). nt=nucleotide position in the ASA cDNA (Stein et al., 1989, J. Biol. Chem., 264:1252–1259. The DNA products and size markers are separated by electrophoresis through 7.5% polyacrylamide gels. (B) DNA from buccal cells of three other individuals (d, e and f), amplified and treated with restriction enzymes and analyzed as in A. (C) Summary of the DNA analysis of the pseudodeficiency mutations of ASA from subjects analyzed in A and B. The presence (+) or absence (−) of the mutation at each site is indicated for the two alleles.

DETAILED DESCRIPTION OF THE INVENTION

Figure 1:
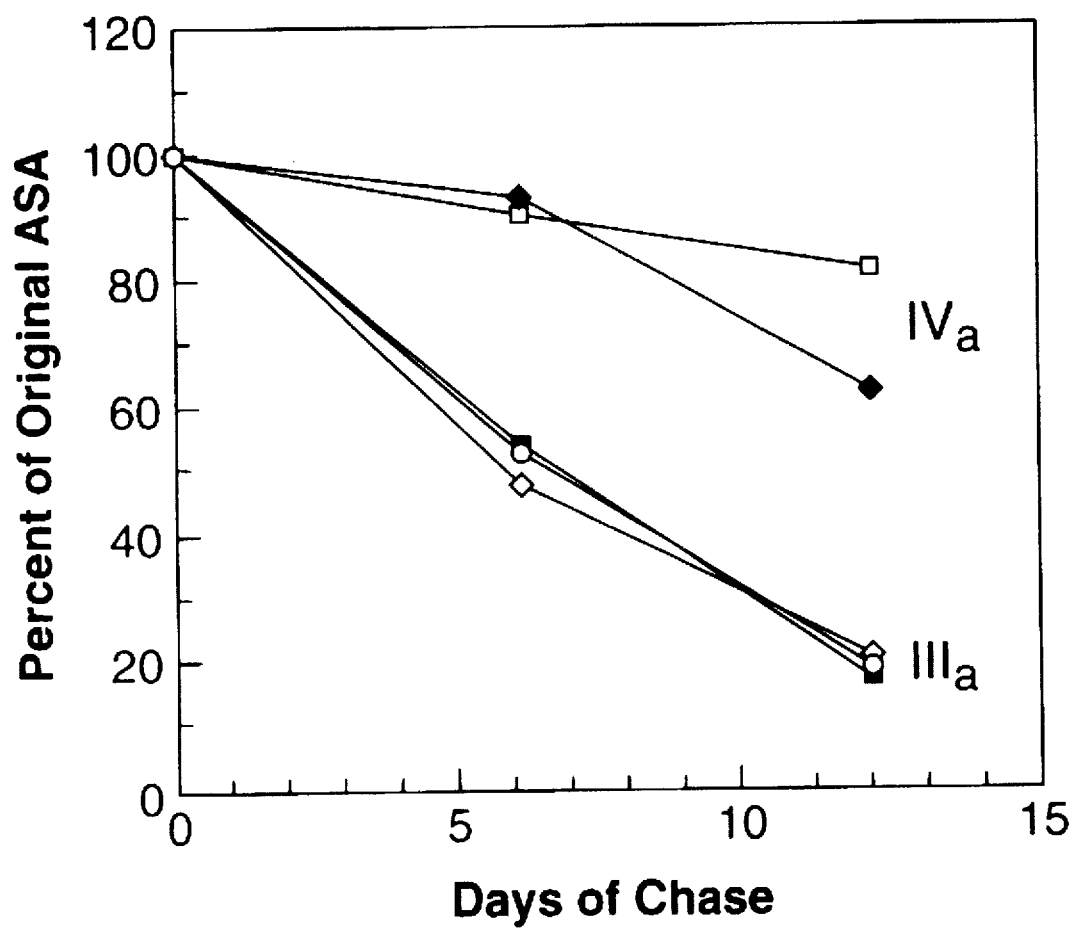
FIG. 1. Catabolic loss of $^{35}$S-methionine-labeled ASA. Fibroblasts from individuals exhibiting $IV_a$ and $III_a$ ASA were grown in culture media containing $^{35}$S-methionine for 18 hours. The radiolabeled proteins were chased with media containing non-radioactive methionine for 0, 6, and 12 days, and the cells were harvested. ASA was immunopurified, identified by SDS-PAGE, and the resulting autoradiograms were quantified by densitometry. Each curve represents data from a single subject with either $III_a$ or $IV_a$ ASA. Each data point was derived from two or three separate experiments.

In its broadest aspect, the present invention is based on the discovery that mutations characteristic of pseudodeficiency (PD) of the arylsulfatase A (ASA) gene are indicative of susceptibility to alcoholism or to the pathological effects of alcohol, or both. In particular, the occurrence of homozygosity for this abnormality resulting in expression of ASA lacking the N-glycosylation site at residue 350 is strongly correlated with alcoholism. The data presented herein demonstrate that humans who are homozygous for a genetic mutation of ASA that results in absence of an N-linked glycan at amino acid residue 350 of ASA are approximately 8 to approximately 18 times more likely to be found with alcoholics than non-alcoholic individuals.

In addition to the mutation resulting in absence of an N-linked glycan in ASA, a second mutation in the polyadenylation signal site of ASA results in greatly decreased expression of the enzyme. This mutation has been found to occur in tight linkage with the mutation that results in absence of the N-linked glycan. However, the N-glycoyslation site mutation may occur in the absence of the polyadenylation signal sequence mutation.

Population studies in Australia, Germany, and Israel indicate that at least 1% of the population carries this mutation. These figures correspond to 2.5 million individuals in the United States, and over 45 million individuals throughout the world. Thus, the present discovery of a correlation between incidence of this genotype and susceptibility to alcoholism, or to the pathological effects of alcohol, is an important advance in health.

Identification and counselling of these individuals would be valuable in order to limit the incidence of alcoholism. The present invention advantageously addresses a longstanding need to identify the genetic components of alcoholism, both to provide for testing that may help to prevent the onset of this insidious disease or characterize the basis of alcoholism in an individual.

As used herein, a mutation in a residue 350 N-glycosylation site of at least one allele of ASA refers to an adenosine to guanosine transition at the nucleotide corresponding to position 1049 of the ASA cDNA. This mutation creates a new BsrI restriction endonuclease site in the mutant ASA gene.

As used herein, a mutation in a polyadenylation signal sequence of at least one allele of ASA refers to an adenosine to guanosine transition at the nucleotide corresponding to position 1620 of the ASA cDNA. This mutation creates a new MaeIII restriction endonuclease site in the mutant ASA gene.

As used herein, the term "alcoholism" refers to an addictive disease or disorder characterized by an inability to control the intake of alcohol, i.e., a continued excessive or compulsive use of alcoholic drinks. Alcoholism may involve changes in the individuals ability to metabolize alcohol as well. Diagnosis of alcoholism presently can be made by psychiatric examination according to the criteria of DSM-III, axis 1 diagnosis of alcohol dependence, abuse, deterioration, or amnestic disorder (see Hulyalkar et al., 1984, Alcoh.: Clin. Exp. Res. 8:337–341).

In addition to clinical alcoholics, the invention relates to identifying individuals who are more susceptible to the pathological effects of alcohol. Although not intending to be limited to any particular theory or hypothesis, it is presently believed that the PD mutation of ASA may contribute to adverse effects of alcohol in some individuals.

Substantial evidence exists for the genetic predisposition of individuals to alcoholism (Devor & Cloninger, 1989, Annu. Rev. Genet., 23:19–36). The underlying genetic and biochemical factors contributing to the neuropathology and addiction pathway of this condition, however, are not understood. Post-mortem analysis of the brains of alcoholics show dysmyelination and a disproportionate loss of cerebral white matter as compared to those of non-alcoholic individuals (Harper et al., 1985, Brit. Med. J. 290:50–504; de la Monte, 1993, ARch. Neurol. 45:990–992; Jensen & Pakkenberg, 1993, Lancet 342:1201–1204). Furthermore, some alcoholic subjects show neurosymptomatology strikingly similar to metachromatic leukodystrophy (MLD) patients. These include neuropsychological deficits in spatial abilities (Manowitz, et al., 1978, J. Nerv. Ment. Dis. 166:500–506) and enlarged cerebral ventricles (Skomer et al., 1983, Arch. Neurol. 40:354–355; Wilkinson and Carlen, 1980, The Biological Effects of Alcoholism, 126:683–699). In late-onset MLD, the initial symptoms include attentional difficulties, hyperactivity, impulsivity, poor judgement, and emotional lability (Shapiro et al., 1994, Neurology 44:662–665), symptoms which often have been associated with alcoholism. MLD patients display a characteristic demyelination pathology resulting from increased levels of sulfatides. This glycolipid comprises a significant proportion of the myelin sheath and accumulates in oligodendrocytes and Schwann cells of individuals with MLD. Since ethanol is known to affect numereous cellular processes and structures (Stibler and Borg, 1991, Scand. J. Clin. Lab. Invest. 51:43–51; Tuma and Sorrell, 1988, Semin. Liver Dis. 8:69–80; Preedy et al., 1990, Alcohol.: Clin. Exp. Res. 14:165–168), including the glycolipid composition of membranes (Rawat, A. K., 1974, Res. Commun. Chem. Pathol. Pharm. 8:461–469; Beauge et al., 1985, Alcohol: Clin. Exp. Res. 9:322–326), a relationship between abnormal sulfatide metabolism and alcoholism may exist.

As used herein, the term "susceptible to alcoholism" refers to an increased likelihood of alcoholism relative to the general population; the term "susceptible to the pathological effects of alcohol" refers to an increased inability to properly metabolize alcohol, or to increased damage, in particular to the nervous system, from ingestion of alcohol. The marker of the present invention is not all inclusive; some individuals diagnosed with alcoholism lack the marker. Also, the marker is highly indicative, but not absolute: a few (about 0.5%) individuals are homozygous for the PD ASA allele but are not diagnosed as alcoholic. (This observation, however, does not exclude the possibility that these "false-positive" individuals have a predisposition toward alcoholism, but simply have not yet developed the disease.)

The present invention provides methods and kits for detecting the presence of the mutations that are indicative of a predisposition to alcoholism or the pathological effects of alcoholism. The immunochemical analytical techniques of the invention are particularly useful for detecting ASA mutants that lack the N-linked glycosylation site at residue 350.

The invention further provides molecular biological techniques that can be used to detect the presence of both the N-glycosylation site mutation and the polyadenylation signal sequence mutation, and discriminate between individuals who may be homozygous or heterozygous for these mutations. These techniques are much simpler and more sensitive than the biochemical techniques previously used to characterize the phenotype of the PD mutation of ASA.

Finally, traditional biochemical techniques indicative of differences between the natively glycosylated and mutant forms of ASA, e.g., denaturing polyacrylamide gel electrophoresis with detection by immunoblotting, can also be used to identify those individuals who carry the PD mutation that results in absence of an N-linked glycan.

The invention advantageously provides kits for detecting the PD mutation in ASA based on the immunochemical analytic techniques and molecular biological analytical techniques of the invention.

Immunochemical Analysis

An epitope characteristic of an N-glycosylation mutation.

As discussed above, one of the mutations characteristic of pseudodeficiency of ASA results in substitution of a serine residue for an N-glycosylated asparagine residue in residue 350 of ASA. Consequently, the mutant ASA lacks one of the N-linked glycans characteristic of the native ASA protein.

According to the invention, mutant ASA lacking an N-linked glycan at position 350 has a unique antibody epitope that is not present on the native (normal) ASA molecule. An antibody specific for this epitope can be blocked from binding to native ASA by steric hindrance: the large glycan group present at this position of ASA in the native protein can prevent or significantly inhibit binding of an antibody specific for the non-glycosylated site.

Accordingly, the present invention advantageously provides antibodies specific for the non-glycosylated epitope, that do not cross react with the native ASA protein. Such antibodies are particularly advantageous, as immunochemical screening assays are fast and relatively easy to perform. As discussed in greater detail infra, the antibodies of the invention are particularly useful for preparing diagnostic test kits, that can be used in physician's offices as well as sophisticated diagnostic laboratory settings.

Methods for obtaining antibodies.

According to the invention, a peptide having an amino acid sequence corresponding to ASA in the region of amino acid residue 350, in which amino acid residue 350 is serine (rather than an N-glycosylated asparagine as in the native molecule) may be used as an immunogen to generate antibodies that recognize ASA lacking this N-glycosylation site, i.e., the product of the mutant ASA PD allele. An antibody reactive with the non-glycosylated form of ASA, and not reactive with the glycosylated form of ASA, is termed herein an antibody specific for the ASA mutant epitope. Such antibodies include but are not limited to polyclonal, monoclonal, chimetic, single chain, Fab fragments, and an Fab expression library.

Various procedures known in the art may be used for the production of polyclonal antibodies to the mutant ASA epitope. For the production of antibody, various host animals can be immunized by injection with the peptide corresponding to the mutant ASA epitope including but not limited to rabbits, mice, rats, sheep, goats, etc. In a preferred embodiment, the peptide is conjugated to an immunogenic carrier, e.g., diphtheria toxoid, bovine serum albumin (BSA), or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the mutant ASA epitope, any technique that provides for the production of antibody molecules by continuous cell lines in culture may be used (see, e.g., Harlow and Lane, *Antibodies: A Laboratory Manual*, Cold Spring Harbor Laboratory Press: Cold Spring Harbor, N.Y.). These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). According to the invention, techniques described for the production of single chain antibodies (U.S. Pat. No. 4,946,778) can be adapted to produce ASA mutant epitope-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for an ASA mutant peptide or mutant ASA itself.

Antibody fragments which contain the idiotype (antigen binding region) of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize the non-glycosylated form of ASA (mutant ASA), one may assay generated hybridomas for a product which binds to the immunogenic peptide corresponding to such epitope. (As is well known in the art, the immunogenic peptide should be provided free of the carrier molecule used in any immunization protocol. For example, if the peptide was conjugated to KLH, it may be conjugated to BSA, or used directly, in a screening assay.)

A polyclonal or monoclonal antibody that reacts with the mutant ASA, or with the peptide corresponding to the mutant ASA epitope, should be tested for cross reactivity with normal (N-glycosylated at residue 350) ASA. Preferably, an antibody of the invention will demonstrate at least 10-fold, more preferably 100-fold, and most preferably greater than 1000-fold, lower binding to the native ASA than mutant ASA, i.e., an antibody of the invention should not cross react significantly with wild type ASA. The difference in binding of antibody to a protein can be evaluated by comparing antibody binding titer, relative affinity, or calculated affinity constants. Preferably, the evaluation is based on antibody binding titer, which is an easily determined empirical value.

The foregoing antibodies can be used in methods known in the art relating to the localization and structure of ASA, e.g., for Western blotting, measuring levels thereof in appropriate biological samples, etc.

The antibodies can be used to detect mutant ASA in a biological sample from an individual. The biological sample can be a biological fluid, such as but not limited to, blood, serum, plasma, interstitial fluid, urine, cerebrospinal fluid, and the like. Preferably, ASA is detected in serum or urine, which are both readily obtained. Alternatively, ASA can be detected from cellular sources, such as, but not limited to, platelets and fibroblasts. For example, platelets or fibroblasts can be obtained from an individual and lysed, e.g. by freeze-thaw cycling, or treatment with a mild cytolytic detergent such as, but not limited to, TRITON X-100® octylphenoxypolyethoxyethanol digitonin, NONIDET P (NP)-40® nonylphenyl-polyethylene glycol, saponin, and the like, or combinations thereof (see, e.g., International Patent Publication WO 92/08981, published May 29, 1992). In yet another embodiment, samples containing cells and body fluids can be used.

The biological samples can then be tested directly for the presence of mutant ASA using an appropriate strategy (e.g., ELISA or radioimmunoassay) and format (e.g., microwells, dipstick [e.g., as described in International Patent Publication WO 93/03367, published Feb. 18, 1993], etc.). Alternatively, proteins in the sample can be size separated, e.g., by polyacrylamide gel electrophoresis (PAGE), in the presence or not of sodium dodecyl sulfate, and the presence of mutant ASA detected by immunoblotting (Western blotting). Immunoblotting techniques are generally more effective with antibodies generated against a peptide corresponding to an epitope of a protein, and hence, are particularly suited to the present invention.

Immunochemical assays.

To characterize whether an individual is homozygous for the PD alleles of ASA, heterozygous, or homozygous for normal ASA, an antibody assay of the invention contemplates comparing the amount of ASA bound by an antibody specific for the PD mutant ASA to the amount of ASA bound by an antibody that binds to all forms of ASA, such as a rabbit anti-ASA polyclonal antibody (e.g., rabbit anti-human liver ASA, available from Calbiochem). If the quantity of ASA bound by the antibody specific for the mutant ASA is about the same as the quantity bound by the antibody reactive with all ASA, then the individual is homozygous for the PD alleles. If the amount of ASA bound by the mutant-specific antibody is about half the amount bound by the antibody reactive with all forms of ASA, then the individual is heterozygous. Finally, if the amount of ASA bound by the mutant-specific antibody is much less than the amount bound by the antibody reactive with all forms of ASA, then the individual is homozygous normal.

In a preferred embodiment, the immunoassay of the invention comprises detecting the amount of ASA bound by an antibody by detecting the enzyme activity of ASA itself. Since mutant ASA demonstrates about the same amount of enzyme activity as native ASA, the total amount of enzyme activity directly relates to the quantity of ASA bound by antibody. For example, the mutant-specific antibody and the antibody specific for all forms of ASA can be separately affixed to solid phase supports, e.g., wells of a microtiter plate, or a solid adsorbent. A biological sample can be contacted with the bound antibody. The amount of ASA that binds to the antibody can be directly detected using an assay for ASA enzymatic activity. In a specific embodiment, the colorimetric substrate p-nitrocatachol sulfate can be used to indicate the presence of ASA (see Manowitz et al., 1981, Biol. Psychiat. 16:1107–13).

In another embodiment, a sandwich immunoassay format using ELISA detection can be used. Accordingly, a first antibody can be attached to a solid phase support, e.g., the wells of a microtiter plate. This first antibody can bind to (capture) ASA in the sample. A second labeled antibody can be used to detect the presence of ASA captured by the first antibody. Either of the first or second antibody (but not both) can be an antibody of the invention, i.e., specific for mutant ASA. The other antibody should bind both forms of ASA.

Alternatively, an competitive assay format can be used. Inhibition of binding of a labeled antibody specific for the mutant epitope of ASA to a peptide corresponding to the ASA mutant epitope (or vice versa) by sample is indicative of the presence of mutant ASA in the sample.

For example, a solid phase assay system may comprise the solid substrate with either bound antibody and labeled mutant ASA peptide or bound mutant ASA peptide and labeled antibody, in which the antibody is specific for the mutant ASA epitope. A sample to be assayed is then placed in contact with the bound and unbound reagents. A competitive reaction between the labeled material and any unlabeled mutant ASA in the sample will prevent the retention of a concentration dependent quantity of the former on the solid substrate, whereupon it can be precisely quantitatively identified, either by detecting an increase in the amount of the label in the liquid phase (unbound to the solid phase), or detecting a reduction in the amount of labeled reagent bound to the solid phase.

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope.

Molecular Biological Analysis

The mutations characteristic of ASA pseudodeficiency can be identified using molecular biological techniques. In particular, the mutation of adenosine to guanosine at the nucleotide corresponding to position 1049 in the cDNA sequence and the mutation of adenosine to guanosine at the nucleotide corresponding to position 1620 of the cDNA sequence can be detected using highly specific oligonucleotide probes, creation of unique restriction endonuclease sites, or combinations thereof. Any of the standard techniques in molecular biology for detecting such mutations, including Southern analysis, Northern analysis, and dot hybridization with specific oligonucleotide probes under conditions of relatively high temperature and hybridization stringency, and the powerful polymerase chain reaction-based analytical techniques, can be used according to the invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

If appearing herein, the following terms shall have the definitions set out below.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along one of the strands. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. According to the present invention, the highest stringency hybridization for the length of the oligonucleotide probe to be used is required since hybridization of the probes must differentially detect sequences with a single base mutation.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

A particular advantage of the present invention is that it can be performed with buccal cells, which are easily obtained using a non-invasive procedure. This greatly reduces the level of discomfort that an individual may suffer and avoids the need for phlebotomy, as well as eliminates the likelihood of infection that accompanies more invasive procedures.

In preferred aspects, genomic DNA or mRNA is amplified by PCR, and the amplified DNA is tested for the presence of the mutation. PCR amplification is well known in the art (Cameron et al., 1992, Science 257:383–387; Saksela et al., 1994, Proc. Natl. Acad. Sci. U.S.A. 91:1104–1108). For example, mRNA can be detected by reverse transcriptase-initiated PCR (see, e.g., Saksela et al., 1993, J. Virol. 67:7423-27). PCR can be carried out, e.g., by use of a Perkin-Elmer Cetus thermal cycler and Taq polymerase (Gene Amp™, Boehringer Mannheim). The amplified PCR products can be analyzed by immobilizationon membranes and hybridization with specific oligonucleotide probes, or by treatment with specific endonucleases and analysis of the products by gel electrophoresis. Labeling of the cleaved PCR products can be accomplished by incorporation of radiolabeled nucleotides, endlabeling, e.g., with $\gamma^{32}$P-ATP, or by staining with ethidium bromide. The present invention provides specific preferred examples of PCR-based analysis of ASA mutations: one, in which genomic DNA (or mRNA) is amplified, and the presence of a restriction site unique to the mutant gene is determined; and a second, in which the genomic DIX1A (or mRNA) is amplified and the mutation detected by binding of specific oligonucleotide probes. DNA from any available source can be used for the PCR-based analysis. Sufficient DNA can be obtained from a finger-prick or from saliva-born buccal cells.

PCR amplification and detection of unique restriction endonuclease sites.

The present invention provides primers for PCR amplification of a segment (preferably about 200 nucleotides in length) of genomic DNA corresponding to the ASA gene or a portion thereof containing the mutated nucleotide; or primers for reverse transcriptase-PCR of mRNA encoding the ASA gene; and a restriction endonuclease specific for a restriction site that is unique to either the mutant ASA gene (and is not found in the native ASA gene), or a restriction site that is unique to the native ASA gene (and is not found in the mutant ASA gene).

It has been discovered that the mutation leading to replacement of Asn$_{350}$ with Ser results from an A to G transition, which creates a new BrsI restriction endonuclease site in the ASA gene. It has also been discovered that the mutation in the polyadenylation site resulting from an A to G transition creates a new MaeIII restriction endonuclease site in the ASA gene. By amplifying a portion of the ASA gene containing the mutated nucleotide, and subsequently treating the amplified product with the restriction endonuclease, the presence of the mutation can be determined by cleavage of the amplified DNA into new fragments that are not formed upon endonuclease treatment of DNA from the native ASA gene. These fragments can be detected readily simply by size on an agarose or polyacrylamide gel. The fragments can be labeled with radionucleotides during PCR amplification, or alternatively detected by ethidium bromide or silver staining. The presence of fragmented DNA indicates that the individual from whom the DNA was originally obtained is homozygous for the PD mutation of ASA; presence of fragmented DNA and unfragmented DNA indicates that the individual from whom the DNA was originally obtained is heterozygous for the PD mutation of ASA; and the presence of only unfragmented DNA indicates that individual from whom the DNA was originally obtained is homozygous for the normal ASA allele.

In a specific example, infra, the invention provides a 5' primer having the sequence TGATGGCGAACTGAGT-GACT (SEQ ID NO:9) and a 3' primer having the sequence AAGGATCTGGGATCAGGGGT (SEQ ID NO:10), to amplify about a 200 nucleotide region of the ASA gene in proximity to the mutation at the nucleotide corresponding to number 1049 of the cDNA sequence. As note above, the mutation at this site results in introduction of an BsrI endonuclease restriction site.

Alternatively, the invention provides a 5' primer having the sequence AGCTTGCTGCCATTGCCCA (SEQ ID NO:11) and a 3' primer having the sequence CATTAC-CCCAGGATTGGTCGAA (SEQ ID NO:12), which primers amplify an approximately 182 nucleotide fragment that contains the polyadenylation signal mutation at the nucleotide corresponding to number 1620 of the cDNA sequence. As noted above, the mutation at this site results in introduction of a MaeIII restriction site.

Most preferably, both sets of primers and restriction endonucleases are used to detect either or both mutations in an ASA allele.

PCR amplification and hybridization of specific probes.

In another embodiment, the invention provides primers for amplifying a segment of genomic DNA corresponding to the ASA gene or a portion thereof containing the mutated nucleotide; or primers for reverse transcriptase-PCR of mRNA encoding the ASA gene; and a labeled oligonucleotide probe for hybridizing to amplified DNA and detecting the presence of a mutation in the ASA gene at a position corresponding to nucleotide 1049 of the cDNA, or nucleotide 1620 of the cDNA, or both. In a specific embodiment, infra, the oligonucleotide probes AAGGTGACAT-TGGGCAGTGG (SEQ ID NO:5) (specific for the native ASA gene around the nucleotide corresponding to position 1049 of the cDNA) and AAGGTGACACTGGGCAGTGG (SEQ ID NO:6) (specific for the mutant ASA gene around the nucleotide corresponding to position 1049 of the cDNA) can be hybridized to the amplified sequence, wherein hybridization of the former probe at 55° C. with washing at 62° C. is indicative of a normal ASA allele, and hybridization of the latter probe at 55° C. with washing at 60° C. is indicative of a PD allele. Alternatively, the oligonucleotide probes CTGGTGTTATTACGTTATC (SEQ ID NO:7) (specific for the native ASA gene around the nucleotide corresponding to position 1620 of the cDNA) and CTGGT-GTTACTACGTTATC (SEQ ID NO:8) (specific for the mutant ASA gene around the nucleotide corresponding to position 1620 of the cDNA) can be hybridized to the amplified sequence, wherein hybridization of the former probe at 48° C. with washing at 52° C. is indicative of a normal ASA allele, and hybridization of the latter probe at 48° C. with washing at 52° C. is indicative of a PD allele. These probes are full described in a reference by Gieselmann et al. (1989, Proc. Natl. Acad. Sci. U.S.A. 86:9436–9440).

In another aspect, the invention provides for detection of the mutated nucleotides in PCR-amplified fragments of the ASA gene by immobilization of the amplified DNA on nitrocellulose or Nylon membranes, and hybridization with labeled oligonucleotide probes complementary to the normal or mutated sequence, a technique known as dot-hybridization analysis. The oligonucleotide probes could be radio-labeled (e.g., with $^{32}$P nucleotides) or non-radioactively labeled (e.g., with digoxygenin), in which case detection of hybridization is by an enzyme-linked color reaction, or, preferably, by chemiluminescence detection.

Biochemical Analysis

As noted above, absence of an N-linked glycan from mutant ASA results in detectable differences in biochemical characteristics related to the extent of glycosylation of the mutant ASA compared to native ASA. The most obvious difference is in electrophoretic mobility. In particular, PD mutant ASA has an apparent molecular weight of about 59 kD by PAGE, whereas normal ASA has an apparent molecular weight of 62 kD under identical electrophoretic conditions.

In another aspect, greater mobility difference is observed upon PAGE analysis between endo-N-acetlyglucosaminidase H (endo-H) treated mutant ASA and normal ASA. For example, a greater loss of mass is detected with ASA from a normal subject upon endo-H treatment (4 kD) than from ASA from a PD subject (1 kD). Such a difference in mass would not be expected in the absence of a difference in the extent of glycosylation between the mutant and normal forms of ASA.

Generally, any assay that can distinguish between native ASA, which contains two N-linked glycan moieties, and mutant ASA, which lacks one of the N-linked glycan moieties, can be used to identify individuals who are homozygous for PD mutant ASA. For example, an assay that directly measures the presence or quantity of N-linked glycans on a protein can be used to detect mutant ASA.

As with the immunoassays described above, the presence of normal ASA should be evaluated in the biochemical assays. If no normal ASA is detected, but only mutant ASA, then the individual is homozygous for the PD mutation. However, if both normal and mutant ASA are present in a sample, the individual is heterozygous, and if only normal ASA is detected, the individual is homozygous normal.

As with the immunoassays, biochemical assays can be used to detect mutant ASA in a biological sample from an individual. The biological sample can be a biological fluid, such as but not limited to, blood, serum, plasma, interstitial fluid, urine, cerebrospinal fluid, and the like. Preferably, ASA is detected in serum or urine, which are both readily obtained. Alternatively, ASA can be detected from cellular sources, such as, but not limited to, platelets and fibroblasts. Platelets or fibroblasts can be obtained from an individual and lysed, e.g., by freeze-thaw cycling, or treatment with a mild cytolytic detergent such as, but not limited to, TRITON X-100®, digitonin, NP-40®, saponin, and the like, or combinations thereof (see, e.g., International Patent Publication WO 92/08981, published May 29, 1992). The cellular lysates can then be assayed directly, with detection of ASA bands by an ASA-specific colorimetric enzyme assay on native (non-denaturing) PAGE, or by Western analysis of proteins separated by SDS-PAGE. Alternatively, ASA in the sample can be enriched by affinity purification or immunoadsorption of ASA present in the sample, followed by PAGE with detection of total protein, ASA enzyme activity, or immunoblotting. Chemical analysis for the presence of N-linked glycans can also be used to determine the biochemical characteristics of ASA in the sample after affinity purification or immunoadsorption.

Kits

The present invention advantageously provides specific kits for use in locations ranging from a physician's office to a sophisticated medical laboratory. The kits of the invention provide reagents necessary to determine whether an individual is homozygous for the PD mutation of ASA, and thus, to evaluate whether the person may be susceptible to alcoholism.

The kits of the invention fall into two categories: kits for immunoassays to detect the presence of mutant ASA; and kits to detect mutations in the genomic DNA or mRNA encoding ASA.

Imunoassay test kits.

An immunoassay test kit may be prepared for the demonstration of mutant ASA in a sample, comprising:

(a) an antibody specific for the mutant epitope of ASA, as described above;

(b) an antibody specific for all forms of ASA; and (c) means for quantitating binding of the antibody specific for the mutant epitope and the antibody specific for all forms of ASA to ASA in a sample from an individual.

The means for detecting binding of the antibody to mutant ASA in a sample from an individual can comprise any of the immunoassay strategies and formats described above.

In a preferred aspect of the invention, the antibody specific for the ASA mutant epitope is a monoclonal antibody generated in mice against the peptide Ac-Cys-Ala-Pro-Leu-Pro-Ser-Val-Thr-Leu-Asp-Gly-Phe-Asp-NH$_2$ (SEQ ID NO:13).

In addition to an antibody and means for detecting binding of antibody to mutant ASA in a sample, an immunoassay kit of the invention may further comprise other reagents and, optionally, directions for use of said kit.

Kits to detect mutations in the genomic DNA or mRNA encoding ASA.

In another embodiment, the invention provides test kits for detecting the presence of a PD mutation in the ASA alleles in an individual. In one embodiment, the kit provides for detecting the mutation in the codon encoding asparagine, which after an A to G mutation encodes serine in the mutant ASA. In another embodiment, the kit provides for detecting the mutation in the polyadenylation signal of the ASA gene. In a preferred embodiment, a test kit of the invention provides for detecting both mutations.

Accordingly, a test kit of the invention may comprise:

(a) primers for amplifying a segment of genomic DNA corresponding to the ASA gene or a portion thereof containing the mutated nucleotide; or primers for reverse transcriptase-PCR of mRNA encoding the ASA gene;

(b) a labeled oligonucleotide probe for hybridizing to amplified DNA and detecting the presence of a mutation in the ASA gene at a position corresponding to nucleotide 1049 of the cDNA, or nucleotide 1620 of the cDNA, or both.

Such a kit may further comprise instructions relating to the appropriate hybridization conditions and temperature; hybridization solution (in lyophilized, concentrated, or correct strength) for use in hybridizations; a membrane for blotting the amplified DNA; reagents for labeling the oligonucleotide probes (e.g., $^{32}$P-labeled nucleotides or digoxygenin); and other reagents.

In another embodiment, a kit of the invention comprises (a) primers for PCR amplification of a segment (preferably about 200 nucleotides in length) of genomic DNA corresponding to the ASA gene or a portion thereof containing the mutated nucleotide; or primers for reverse transcriptase-PCR of mRNA encoding the ASA gene;

(b) a restriction endonuclease specific for a restriction site that is unique to either the mutant ASA gene (and is not found in the native ASA gene), or a restriction site that is unique to the native ASA gene (and is not found in the mutant ASA gene).

Preferably, such a kit incorporates the primers and restriction endonucleases specifically disclosed above, and exemplified in Example 2, infra. Such a kit may further comprise instructions relating to the appropriate amplification conditions and endonuclease cleavage conditions; gels for electrophoresis of the PCR products; and other reagents. Optionally, the kit may provide reagents for detecting the amplified DNA, e.g., ethidium bromide, or a labelled nucleotide triphosphate (e.g., $^{32}$P-thymidine, adenosine, or cytosine) for incorporation in the amplified DNA.

The invention may be more completely understood by reference to the following non-limiting example, which is provided solely as an example of a specific embodiment of the invention.

EXAMPLE

THE ASSOCIATION OF ALCOHOLISM WITH THE N-GLYCOSYLATION POLYMORPHISM OF PSEUDODEFICIENT HUMAN ARYLSULFATASE A

This Example concerns the discovery that the $III_a$ and $III_b$ electrophoretic variants of arylsulfatase A (EC 3.1.6.8) are twelve-times more prevalent in alcoholic than in non-alcoholic populations. These variant enzymes, found in almost exclusively a subset of alcoholics, possess the pseudodeficient $Asn_{350}$-Ser mutation of arylsulfatase A and, consequently, lack an N-linked glycan unit. Individuals expressing these genetically determined variants of arylsulfatase A show reduced enzymic activity and intracellular half-life. We hypothesize that ethanol causes an increase in the pools of sulfatides, the substrate for arylsulfatase A, and that individuals who have greatly reduced levels of arylsulfatase A are less capable of maintaining acceptable steady-state levels of this glycolipid. The consequence of this interaction would be to cause neuropathological symptoms common to metachromatic leukodystrophy patients and some alcoholic individuals, and/or influence the addiction pathway of alcoholism by impacting on sulfatide-associated neurotransmitter systems.

Materials And Methods

Enzyme assays.

ASA (Manowitz et al., 1981, Biol. Psychiat., 16:1107), β-galactosidase (Gorman & Poretz, 1987 *J. Cell. Physiol.* 131:158–164), and β-hexosaminidase activities (Gorman and Poretz, supra) and total protein (Manowitz et al., 1981, supra) were measured as described previously.

Analysis of variant banding pattern.

Platelet ASA isoform patterns from each individual was determined by non-denaturing PAGE according to Hulyalkar et al. (1984, Alcoh.: Clin. Exp. Res. 8:337–341).

Genetic analysis for PD ASA polymorphisms.

Genotyping was performed as described previously (Gieselmann et al., 1989, Proc. Natl. Acad. Sci. U.S.A. 86:9436–9440) with modifications. Two polymerase chain reaction (PCR) products were amplified using primers, 5'-TTGATGGCGAACTGAGTGAC-3' (SEQ ID NO:1) and 5'-CGAAGCACTGCACATACCTGG-3' (SEQ ID NO:2), for the N-glycosylation site, and primers, 5'-GCTCTATGACCTGTCCAAGGACC-3' (SEQ ID NO:3) and 5'-TTCCTCATTCGTACCACAGG-3' (SEQ ID NO:4), for the polyadenylation signal consensus sequence site. One µg of DNA, isolated from fibroblasts was amplified in the PCR buffer containing 1.5 mM MgCl$_2$ (Perkin Elmer Cetus). After an initial denaturation period of 5 min at 95° C., forty amplification cycles were performed with the following conditions: annealing period of 1 min at 55° C., an elongation period of 1 min at 72° C., and a denaturation period of 30 sec at 94° C. Final extension was performed for 4 min.

Determination of rates of degradation.

Monolayers of fibroblasts, grown to confluency in 75 cm$^2$ flasks or round petri plates (9.6 cm$^2$), were exposed to Dulbecco's Modified Eagle Medium (DMEM) lacking methionine (Gibco BRL) for 1 hour, followed by 18 hours in the same medium containing Trans $^{35}$S label (>1000 Ci/mmol, ICN Biomedical). The media for fibroblasts from $III_a$ individuals contained 300 µCi $^{35}$S, and for cells from $IV_a$ individuals, 150 µCi $^{35}$S in 4 ml of DMEM lacking methionine supplemented with 2 mM glutamine, penicillin (50 IU/ml), streptomycin (50 µg/ml) and 5% dialyzed fetal calf serum. Four ml (75 cm$^2$ flask) or 1.0 ml (round petri plate) of this solution was added to the cells. Following 18 hours, the radioactive medium was replaced with Eagle's Modified Essential Media (Mediatech Inc.) lacking radiolabeled methionine. Fresh medium was applied every three days. Cells of each sample were washed twice with a 0.25M sucrose containing 5 mM HEPES, buffered at pH 7.1. The cells were lysed with 220 µl of 10 mM Tris/HCl, pH 7.5 buffer containing 0.15M NaCl and 0.8% TRITON X-100. Alternatively, the cells were harvested as described previously (20). All preparations were clarified by centrifugation at 20,000×g for 25 min, pre-adsorbed twice with 30 µl Gamma bind G agarose (Pharmacia) coated with control rabbit serum, and immunoadsorbed with 15 µl Gamma Bind G beads coated with IgG from rabbit anti-human liver ASA or rabbit anti-human cathepsin serum (Calbiochem). The antigen was extracted from the immunoadsorbant as per the manufacturer's instructions and subjected to SDS-PAGE (8% acrylamide for ASA or 10% acrylamide for cathepsin D).

Determination of rates of synthesis.

Rates of synthesis of enzymes were determined in a manner similar to the rates of degradation except for the following: 300 µCi of Trans-$^{35}$S-methionine in 2 ml of labeling solution supplemented with 10 mM NH$_4$Cl was added to each 25 cm$^2$ flask and the cells were grown in labeling medium for 2–10 hours; medium containing the radiolabeled protein was dialyzed in 10 mM Tris/HCl, pH 7.5 buffer containing 0.15M NaCl before immunopurification of the ASA and cathepsin D.

Results And Discussion

Distribution of ASA Variants in Alcoholic, Psychiatric, and Normal Populations.

Alcoholic individuals and non-alcoholic, psychiatric patients, both of whom were inpatients at the Lyons Veterans Administration Medical Center, as well as healthy subjects, without any present medical illness or past/present psychiatric illness, were screened for the presence of electrophoretic ASA variants. As shown in Table 1, 6.6% of the alcoholic patients presented $III_a$ or $III_b$ electrophoretic variants of the enzyme, whereas only one individual in the healthy population (0.6%) and one psychiatric subject (0.5%) were detected with such variants. The alcoholic population of 151 patients included 10 individuals with $III_a$ or $III_b$ variant ASA, but only one of the 164 healthy subjects had one of these variants (Fisher's Exact Test, two tail method, p=0.004). No significant difference was found in the prevalence of these variants in the psychiatric population as compared to the healthy group. The incidence of the $III_a$ variant in the alcoholic population (4.6%) is eight-fold that found in the healthy (0.6%) and nine-fold the level in the psychiatric (0.5%) populations. Individuals with the $III_b$ variant ASA were found only in the alcoholic population. The psychiatric patients served as a control group who were hospitalized, but were not alcoholic. Accordingly, differences which distinguish the alcoholic population from the normal and psychiatric groups would be expected to relate to conditions associated with alcoholism.

TABLE 1

Distribution of ASA variants in alcoholic, psychiatric, and healthy populations

| 5 | Number of individuals expressing each ASA isoform pattern | | | Percent of population with $III_a$ or $III_b$ |
|---|---|---|---|---|
| | $III_a$ | $III_b$ | other | variant ASA |
| Alcoholic patients | 7 | 3 | 141 | 6.6% (10/151) |
| Psychiatric patients | 1 | 0 | 217 | 0.5% (1/218) |
| Normal subjects | 1 | 0 | 163 | 0.6% (1/164) |

Notes To Table 1.

Variant isoform patterns for each subject was determined by PAGE analysis of platelet ASA. Diagnoses were made by the independent examination of individuals by two psychiatrists according to the criteria of DSM-III, axis 1. The patients of the alcoholic population were diagnosed with alcohol dependence n=139), alcohol abuse (7), dementia associated with alcoholism (3), and alcohol amnestic disorder (2). The subjects of the non-alcoholic psychiatric population were diagnosed with schizophrenia (169), bipolar disorder (12), dysthymic disorder (9), substance (excluding alcohol) abuse (7), personality disorders (5), major depressive episode (5), anxiety state (3), paranoid disorders (2), dissociative disorder (1), primary degenerative dementia (1), epilepsy (1), Huntington's chorea (1), tuberous sclerosis (1), and brief reactive psychosis (1). The results presented in this table include data from a previous study (21). The mean averages of the ages (±S.D.) of the alcoholic, psychiatric, and normal control populations were: 43.1 (±11.8), 39.0 (±12.4), 33.4 (±11.6). The sex distributions of the same groups were: 149 males, 2 females; 202, 16; 150, 14. The race distributions of the same groups were: 119 white, 32 black, 0 oriental; 177, 41, 0; 132, 31, 1. Informed consent was obtained from each subject after the nature and possible consequences of the study was explained.

Relationship of variant ASA with PD-ASA.

We recently reported that the expression of a variant form of ASA in fibroblasts parallels that in platelets for an individual (Park et al., 1993, FASEB J. 7:744 (abstract)). In addition, the $III_a$ enzyme lacks one of the two N-glycan moieties present in the $IV_a$ form of ASA which predominates in the general population (Park et al., supra). In view of these results, studies were undertaken to determine if the electrophoretic variants are related to PD-ASA. The enzymic activity of ASA in fibroblasts of $III_a$ individuals is generally reduced when compared to that expressed by the cells of $IV_a$ subjects (Table 2). In addition, this reduction is specific for ASA since a comparable reduction in other lysosomal enzymes, β-galactosidase and β-hexosaminidase, was not observed. The relative levels of ASA activity in the $III_a$ and PD-ASA subjects are similar to those previously reported for PD-ASA individuals (Kolodny, E. H., 1989, The Metabolic Basis of Inherited Disease, ed., pp. 1721–1750).

TABLE 2

Biochemical characteristics of the ASA protein and gene from individuals with $IV_a$, $III_a$, or $III_b$ electrophoretic variants

| ASA type | Subject | N-glycosylation site polymorphism | Polyadenylation signal site polymorphism | Normalized cellular enzyme activity* | Normalized rate of intracellular degradation* | Normalized rate of synthesis* |
|---|---|---|---|---|---|---|
| $IV_a$ | NU | N/N | N/N | 100.0 (+/− 2.3) | 20.9 (+/− 1.7) | ND |
| $IV_a$ | SQ | N/N | N/N | 79.8 (+/− 2.8) | 12.4 (+/− 2.5) | 100.0 (+/− 17.3) |
| $IV_a$ | QN | N/PD | N/PD | 75.8 (+/− 3.4) | ND | ND |
| $IV_a$ | XX | N/N | N/N | 51.7 (+/− 1.7) | ND | ND |
| $III_a$ | KE | PD/PD | N/N | 39.0 (+/− 1.7) | 81.5 (+/− 5.0) | 97.4 (+/− 16.9) |
| $III_a$ | SE | PD/PD | PD/PD | 18.2 (+/− 0.6) | 93.0 (+/− 6.4) | ND |
| $III_a$ | QE | PD/PD | PD/PD | 16.9 (+/− 0.3) | ND | ND |
| $III_a$ | DH | PD/PD | PD/PD | 14.5 (+/− 0.4) | 100.0 (+/− 2.9) | 43.0 (+/− 10.9) |
| $III_a$ | NH | N/PD | N/PD | 4.3 (+/− 0.1) | ND | ND |
| $III_b$ | KK | PD/PD | N/N | ND | ND | ND |

*mean +/− S.E.M.

Notes To Table 2.

The normalized cellular ASA activity is the enzymic activity relative to the average of the β-galactosidase and β-hexosaminidase activities in a given preparation. The normalized rate of intracellular ASA degradation is the daily rate of loss of $^{35}$S-methionine labeled ASA relative to that rate for cathepsin D. The normalized rate of ASA synthesis is the amount of $^{35}$S-labelled ASA synthesized hourly, relative to that rate for cathepsin D. The values are normalized such that the highest of each set is set at 100. "PD" indicates the presence of the PD polymorphism and "N" the presence of the normal sequence for either the N-glycosylation sequon or polyadenylation signal consensus sequence to of the ASA gene determined by PCR and Southern blot analysis. The nature of each allele for both sites are indicated. ND denotes that values were not determined.

To determine whether the $III_a$ phenotype is equivalent to the PD-ASA genotype, Southern blot analysis of PCR amplified segments of the ASA gene from $III_a$ and $IV_a$ individuals was performed according to Gieselmann et al. (1989, Proc. Natl. Acad. Sci. U.S.A. 86:9436–9440). Probes capable of distinguishing the PD-ASA, A-G transition at the N-glycosylation site, demonstrated that such a mutation exists in both alleles of individuals with the $III_a$ variant but not in those of persons with the $IV_a$ enzyme (Table 2). In addition, the ASA gene from a type $III_b$ individual also possesses the identical PD polymorphism. The consequence of the A-G transition is the loss of a potential N-glycosylation site. Since this site is utilized in the normal allele (Gieselmann et al., supra), it may be concluded that $III_a$ and $III_b$ ASA differ from $IV_a$ by the lack of the $Asn_{350}$-linked glycan. One subject (NH) with a $III_a$ pattern is N/PD at both polymorphic sites. This individual, however, is a brother of an MLD patient and is probably MLD/PD for ASA. Since the product of the MLD allele lacks enzyme activity, the $III_a$ isoform pattern is observed.

As shown in Table 2, most $III_a$ subjects also carried the PD-ASA, A-G transition at the polyadenylation signal consensus sequence of the ASA gene. This mutation, however, does not affect the structure of the polypeptide product. The ASA of subject KE, who lacks this polymorphism, yields a $III_a$ electrophoretic pattern identical to that observed for ASA from subjects who carry the polyadenylation signal mutation.

The biochemical characteristics of PD-ASA have been extensively examined (see Kolodny, 1989, in The Metabolic Basis Of Inherited Disease, Scriver et al. (eds.), McGraw Hill, New York. pp. 1721–50 for review). In light of this, the basis for the reduced cellular ASA activity in $III_a$ individuals was investigated to confirm the PD nature of $III_a$ ASA. Consideration was given to 1) intracellular stability, 2) rate of synthesis, 3) cellular localization, and 4) specific enzyme activity of the enzyme. As shown in FIG. 1 and Table 2, the enzyme for $III_a$ individuals, who are homozygous for the PD N-glycosylation site polymorphism, is at least four times more susceptible to intracellular degradation than is ASA from the $IV_a$ subjects. This includes the $III_a$ subject KE, who is normal at the polyadenylation signal site sequence. The finding that the loss of the $Asn_{350}$-linked glycan is a destabilizing factor for the enzyme is consistent with the conclusions of Ameen and Chang (1987, FEBS Lett. 219:130–134) )on PD-ASA. In contrast, Gieselmann et al. (supra) reported no contribution of the PD N-glycosylation polymorphism to the reduced cellular activity of PD-ASA. The reason for this discrepancy may be related to the use of a transfected BHK expression system (Gieselmann et al., supra) as opposed to human fibroblasts (Ameen and Change, supra).

Studies on the rate of synthesis of ASA in fibroblasts from $III_a$ and $IV_a$ subjects demonstrated that the presence of the polyadenylation signal site consensus sequence polymorphism also has an impact on the steady-state levels of ASA. These studies were performed by quantifying the amount of newly synthesized ASA secreted into the media by cells exposed to $NH_4Cl$. This approach allows for the measurement of the rates of synthesis of lysosomal enzymes under conditions which minimize the concomitant effect of intracellular degradation. As shown in Table 2, the fibroblasts of the $III_a$ subject KE, normal at the polyadenylation signal site, exhibit relative levels of ASA synthesis identical to that of fibroblasts from a homozygous normal $IV_a$ individual, SQ. Cells from the $III_a$ subject DH who possesses the PD-polyadenylation site polymorphism, however, showed only one-half this rate. The impact of the PD polymorphism on the rate of ASA synthesis, as reported here, is more moderate than the ten-fold decrease noted by Gieselmann et al. (supra) but is greater than that observed by Ameen and Chang (supra). Consistent with the conclusion that both PD-ASA polymorphisms affect the steady-state levels of $III_a$ and $III_b$ ASA, fibroblasts of subject KE showed twice the total cellular ASA activity of fibroblasts from subjects who are homozygous for both PD-ASA polymorphisms, and approximately 50% the activity levels of the cells from $IV_a$ subjects.

Since ASA does exhibit, in part, mannose-6-phosphate receptor mediated targeting to lysosomes (Ameen et al., 1990, Mol. Cell. Biochem., 92:117–127), the absence of the N-glycan at aminoacyl residue 350 may potentially affect this process. Subcellular localization of variant ASA was studied employing the double Percoll density fraction approach of Gorman and Poretz (1987, J. Cell. Physiol. 131:158–164). Consistent with the findings of Ameen et al. (supra) on PD-ASA, we detected no significant difference between fibroblasts from $III_a$ and $IV_a$ subjects in regard to the relative distribution of the enzyme in the dense lysosome, light lysosome, endosome, or smooth membrane subcellular fraction of the cells (data not shown). Furthermore, the $Asn_{350}$-Ser conversion and the absence of the associated N-glycan did not affect the enzyme's specific activity (activity of ASA/amount of ASA protein) toward a synthetic substrate (data not shown). ASA activity was quantified using the p-nitrocatechol method of Manowitz et al. (1981 Biol. Psychiat. 16:1107–1113) and the quantity of ASA protein was determined by SDS-PAGE followed by quantitative immunology analysis. Accordingly, the decreased cellular level of ASA in fibroblasts of $III_a$ individuals is not due to a change in specific enzymic activity or mistreating of the enzyme.

Implications for alcoholism.

We have shown that there is a greater prevalence of individuals possessing the $III_a$ and $III_b$ electrophoretic variants of ASA in alcoholics than in psychiatric and healthy controls. As with PD-ASA, these variants exhibit reduced ASA activity, and carry the PD-ASA polymorphism at the N-glycosylation site. Consequently, our population study evidences a strong association of the PD-ASA N-glycosylation polymorphism of ASA and alcoholism. From the work of Nelson et al. (1991, Hum. Genet. 87:87–88) and Hohenshutz et al. (1989, Hum. Genet. 82:45–48), it can be inferred that approximately 2% of the Australian population and 0.5% of the German population, respectively, are homozygous for the N-glycosylation site polymorphism and express the $III_a$ or $III_b$ form of ASA. Based upon the genotype expected for the $III_a$ and $III_b$ variant phenotypes, we estimate that the frequency of individuals homozygous for the PD-ASA N-glycosylation polymorphism is 0.6% in the normal, 0.5% in the psychiatric, and 6.6% in alcoholic populations. This suggests that worldwide, the approximately 25–110 million individuals who exhibit the homozygous N-glycosylation site polymorphism of PD-ASA have a twelve fold greater propensity of being alcoholic, compared to individuals with normal ASA.

The attenuated levels of ASA in individuals expressing the $III_a$ or $III_b$ ASA variant as a result of the PD-ASA genotype is a possible explanation for the observed association of this condition with alcoholic patients. MLD patients who possess 0–5% the ASA activity of normal subjects exhibit 2–50% of the normal ability to degrade sulfatides (Kappler et al., 1991, Hum. Genet. 86:463–470). Individuals who are homozygous for PD-ASA show an ASA activity of 10–30% of normal, but demonstrate a normal sulfatide loading profile (Kappler et al., supra). Those persons who are heterozygous for MLD and PD-ASA, however, show levels of enzymic activity 5–10% that of normal and exhibit a reduced sulfatide catabolism equivalent to 15–75% of that by homozygous normal subjects (Kappler et al., supra). Evidently, the level of ASA activity in homozygous PD-ASA individuals is at a minimal threshhold level which still allows normal sulfatide metabolism. A reduction of ASA activity below this level appears to result in reduced sulfatide catabolism as denoted by the sulfatide loading test. This concept of a critical threshold level of enzyme was presented by Conzelmann and Sandhoff (1984, Dev. Neurosci. 6:58–71) in their theoretical discussion on the correlation between residual enzyme activities in inherited enzyme deficiencies and the development of neurological disorders. Accordingly, factors which have a negative impact on cellular ASA levels or which through an ASA-independent pathway increase sulfatide production, may result in elevated sulfatide pools similar to that observed in MLD patients.

An exciting hypothesis is that exogenous ethanol and/or its metabolites causes increased sulfatide levels by either lowering ASA activity below the critical threshhold level necessary for normal sulfatide catabolism and/or increasing sulfatide production. It is known that alcohol causes abnormal glycosylation (Stipler and Borg, 1991, Scand. J. Clin. Lab. Invest. 51:43–51) and glycoprotein trafficking (Tuma and Sorrell, 1988, Semin. Liver Dis. 8:69–80), and decreased protein synthesis (Preedy et al., 1990, Alcohol.: Clin. Exp. Res. 14:165–168). In addition, chronic ingestion of alcohol by mice results in increased levels of brain sulfatides (Rawat, A. K., 1974, Res. Commun. Chem. Pathol. Pharm. 8:461–469). We suggest that ethanol would cause increased intermittent steady-state levels of sulfatides, potentially reaching pathological levels in $III_a$ or $III_b$ (PD) individuals who possess critical threshhold levels of the enzyme. It is envisioned that varying levels of ethanol in subjects with variants of ASA will result in a cyclical pattern of high and normal levels of sulfatides, eventually resulting in dysmyelination, a form of white matter disease. A consequence of this may be the late-onset MLD-like symptoms observed in some alcoholics.

Interestingly, sulfatides are an integral component of the β-endorphin receptor and appear to be required for receptor activity (Craves et al., 1980, Science 207:75–76). They also are capable of binding both β-endorphin and dynorphin (Wu et al., 1986, J. Biol. Chem. 261:3687–3691). It is intriguing to postulate that ethanol-induced increases in steady-state sulfatide pools may impact upon specific neurotransmitter receptors involved in an ethanol addiction pathway. The consequence of this would be a cyclical ethanol-reinforced addiction which would be more prominent in individuals who have a reduced capacity to buffer levels of sulfatide pools, as may be the case with those who are PD in ASA. Verification of these hypotheses requires the demonstration of the biochemical nature of the impact of ethanol on sulfatide pools.

EXAMPLE 2

A METHOD FOR RAPID DETECTION OF ARYLSULFATASE A PSEUDODEFICIENCY MUTATIONS

Pseudodeficiency of arylsulfatase A is a complicating factor in the determination of metachromatic leukodystrophy risk and carrier status. A method using PCR and restriction enzyme digestion to detect the presence of both the mutations that contribute to arylsulfatase A pseudodeficiency is described using DNA from blood or buccal cells. Application of this technique should facilitate determination of metachromatic leukodystrophy status and counseling in families where the pseudodeficiency allele is present.

Materials and Methods

DNA isolation.

Genomic DNA was isolated from white blood cells by proteinase K digestion and phenol extraction as described (Ausubel et al., 1994, in *Current Protocols in Molecular Biology*, John Wiley and Sons: New York). Buccal cells were collected on a cytology brush and DNA was prepared by heating in 50 mM sodium hydroxide and neutralization with Tris as described (Richards et al., 1993, Hum. Molec. Genet. 2:159–163).

PCR amplification.

Oligonucleotide primers for PCR amplification were designed with the aid of the MacVector program (Eastman Kodak) and obtained from National Biosciences (Plymouth, Minnesota). A 200 base pair fragment spanning the third potential N-glycosylation site at amino acid residue 350 (nucleotide 1049) was amplified with the primers ASA2c (5'-TGATGGCGAACTGAGTGACT) (SEQ ID NO:9) and ASA4nc (5'-AAGGATCTGGGATCAGGGGT) (SEQ ID NO:10) using about 0.5 µg of blood DNA (or 10 µl of the buccal DNA) in 50 mM KCl, 10 mM Tris (pH 8.3), 1.5 mM $MgCl_2$, 200 µM each of dATP, dTTP, dCTP and dGTP and 1.25 units of Taq DNA polymerase. Following an initial denaturation at 95° C. for 3 minutes, amplification was carried out for 35 cycles by denaturation at 95° C. for 30 seconds, annealing at 56° C. for 1 minute and extension at 72° C. for 30 seconds in a 50 µl volume using an MJ Research PTC100 thermal cycler.

A 182 base pair fragment spanning the polyadenylation signal site at cDNA nucleotide 1620 was amplified with primers ASA3c (5'-AGCTTGCTGCCATTGCCCA) (SEQ. ID. NO:11) and ASA5nc (5'-CATTACCCCAGGATTGGTCGAA) (SEQ ID NO:12) using the same conditions described above for the ASA2c/ASA4nc primer pair. However, efficient amplification of the 182 base pair fragment with primers ASA3c and ASA5nc was also achieved using a rapid 2-step cycling program (94° C. for 20 seconds, and 56° C. for 30 seconds for 35 cycles).

Restriction endonuclease treatment and gel electrophoresis.

The 200 base pair fragment is cleaved by the restriction endonuclease BsrI when the N-glycosylation site is mutated, resulting in two fragments of 112 and 88 base pairs. Following PCR amplification the reaction was sequentially extracted with an equal volume of phenol and chloroform and the DNA was ethanol precipitated in the presence of 0.3M sodium acetate. Following a 70% ethanol wash, the pellet was dried and dissolved in 20 µl of 0.1 mM EDTA, 1 mM Tris (pH 8.0). An aliquot (6 µl) of the DNA was digested in a final volume of 25 µl with 10 units BsrI in the buffer provided by the supplier (New England Biolabs) at 65° C. for 3 hours.

The 182 base pair fragment spanning the polyadenylation signal site is efficiently cleaved with MaeIII (Boehringer Mannheim) without the need for organic extraction or ethanol precipitation. A volume of 9.8 µl was digested with 2 units MaeIII in a final volume of 12 µl at 55° C. for 3 hours. In the absence of a mutation the 182 base pair fragment is cleaved to fragments of 153 and 29 nucleotides. When the polyadenylation signal sequence is mutated the 153 base pair fragment is further cleaved to 129 and 24 base pair fragments. All PCR and restriction enzyme digestion products were separated by electrophoresis through 7.5% polyacrylamide gels run in TBE buffer (Ausubel et al., supra) and photographed after staining with ethidium bromide.

Results

Analysis of the ASA genotype using DNA isolated from leukocytes of three individuals is presented in FIG. 2A. Subject 'a' is homozygous normal at both the polyadenylation signal site (nucleotide 1620) and the N-glycosylation site (nucleotide 1049), as the 182 base pair PCR product is reduced to 153 base pairs after treatment with MaeIII, and the 200 base pair fragment spanning the N-glycosylation site is unaffected by treatment with the BsrI. Subject 'b' is homozygous for the presence of the pseudodeficiency mutations at both the polyadenylation signal and N-glycosylation sites, as the 182 base pair product is cleaved to 129 base pairs by MaeIII and the 200 base pair product spanning the mutated N-glycosylation site is completely cleaved to bands of 112 and 88 base pairs by BsrI. Subject 'c' is heterozygous for both sites, having two bands visible in the MaeIII digest (153 and 129 base pairs) and three bands visible in the BsrI digest (200, 112 and 88 base pairs).

FIG. 2B shows an analysis of the ASA genotype using buccal cells from three other individuals as a source of DNA. Subject 'd' is homozygous normal at both sites, subject 'e' heterozygous at both sites and subject 'f' is heterozygous at only the N-glycosylation site. Being able to genotype ASA with DNA from buccal cells means that the sample for analysis can be provided by the subject without discomfort or the need for a phlebotomist, and the entire process of obtaining the sample, DNA isolation, PCR amplification, restriction enzyme digestion and analysis of results can easily be completed in a single day. The genotypes of the subjects analyzed in FIG. 2A and 2B are summarized in FIG. 2C.

Discussion

In the diagnosis of susceptibility to alcoholism and of MLD, and assessment of risk for potential siblings or offspring of individuals carrying these traits, it is important to be able to detect both the pseudodeficiency mutations of ASA in family members of affected persons (Shen et al., 1993, Am. J. Med. Genet., 45:631–637). The method presented in this Example is rapid and provides direct visualization of the ASA genotype at both the pseudodeficiency sites. This is particularly important as the N-glycosylation site mutation can occur in the absence of the polyadenylation signal site mutation (Nelson et al., 1991, Hum. Genet., 87:87–88; Hohenschutz et at., 1989, Hum. Genet., 82:45–48), and the N-glycosylation site mutation does appear to influence the enzyme activity (Shen et al., supra). Furthermore, in some populations the polyadenylation site mutation is not found while the N-glycosylation site mutation is encountered at a gene frequency of more than 0.4.

An alternative method that has been used for the detection of the pseudodeficiency mutations of ASA include immobilization of PCR products on a membrane and sequential hybridization to the products with allele specific radiolabelled oligonucleotide probes (Gieselmann et al., 1989, Proc. Natl. Acad. Sci. U.S.A., 86:9436–9440; Shen et al., supra). This approach is suited to analysis of very large numbers of samples, but is both expensive and time consuming when applied to smaller numbers of individuals, as is typical in family diagnostic studies. Two methods to determine the presence of polyadenylation signal site of ASA at nucleotide 1620 of the cDNA, but not the nucleotide 1049 mutation, have also been described (Gieselmann et al., 1991, Hum. Genet. 86:251–255; Chabas et al., 1993, Clin. Genet. 44:320–323). One is an allele-specific amplification assay requiring the use of three pairs of primers for each analysis (Giesehnann et al., 1991, supra), and the second uses a mismatched primer to produce a RsaI restriction site when the polyadenylation signal mutation is present (Chabas et al., supra). This latter report has overlooked the MaeIII restriction site produced by the polyadenylation signal site mutation.

In summary, the methodology described in this Example enables the rapid and accurate detection of the status of both sites known to contribute to pseudodeficiency of ASA in DNA of individuals. This should facilitate the identification and distinction of MLD and ASA pseudodeficiency alleles in family studies, which is important in order to provide genetic counseling to such families in connection with both susceptibility to alcoholism and the possibility of developing MLD. Furthermore, the techniques described are applicable to larger investigations designed to determine the relative frequency of the pseudodeficiency mutations in different populations.

EXAMPLE 3

AN IMMUNOASSAY FOR PSEUDODEFICIENT ASA

The immunoassay is an enzyme-linked assay to detect the aberrant enzyme in cellular extracts and/or body fluids of individuals. The basis of the assay is to employ an antibody which can react with ASA lacking the glycan at residue 350 and binds with specificity to only ASA possessing this structural abnormality. The reagent is prepared as a monoclonal antibody elicited to a synthetic antigen possessing the oligopeptide structure analogous to the amino acid sequence surrounding residue 350 of ASA containing a serine residue rather than the normal asparagine residue at this location. Hybridomas secreting such an antibody are identified in screening assays by detecting those which exhibit reactivity toward the mutant ASA but lack reactivity towards the normal enzyme.

An oligopeptide, Ac-CAPLPSVTDGFD-NH$_2$ (SEQ ID NO:13) has been prepared synthetically (Chiron Mimotopes, San Diego, Calif.). This peptide is covalently coupled via the —SH group of the amino terminal cysteine to diphtheria toxoid and to bovine serum albumin. The serine residue underlined is the amino acid which differs from the asparagine 350 of normal ASA. humanization of mice and hybridoma preparation is performed by conventional methods employing the oligopeptide-diphtheria toxoid conjugate and the immunogen (see E. Harlow and D. Lane, in *Antibodies: A Laboratory Manual* Cold Spring Harbor Laboratory Press: Cold Spring Harbor, N.Y.).

An antigen capture ELISA assay is employed essentially as described by Harlow and Lane, supra. The detection antigens employed are pseudodeficient ASA (prepared as a partially purified extract from fibroblasts of an individual who is homozygous for the mutant enzyme) or normal ASA (prepared as a partially purified extract from fibroblasts of an individual who is homozygous for the normal enzyme). The presence of bound enzyme in the ELISA is detected employing a colorimetric assay for ASA utilizing p-nitrocatachol sulfate by a method similar to that described by Manowitz et al. (1981, Biol. Psychiat. 16:1107–1113). Alternatively, hybridomas secreting antibody which reacts with the antigenic oligopeptide are detected by an antibody capture ELISA utilizing the oligopeptide conjugated to bovine serum albumin similar to the procedure described by Harlow and Lane, supra. Positive hybridomas identified in this assay are then screened by the antigen capture assay with mutant and normal ASA as described above. Hybridomas which exhibit reactivity with the mutant enzyme but not the normal enzyme are expanded in either tissue culture (see Harlow and Lane) or in vivo (in ascites) as described by Lee and Poretz (1991, Immunol. Cell Biol. 69:15 1–157).

The foregoing examples have been provided for a better understanding of the invention and as an illustrative description presenting the details of the constructs and procedures that were followed in its development and validation. The invention is not intended to be limited to the examples. This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein. It is also to be understood that all base pair sizes given for nucleotides and all molecular weight information for proteins are approximate and are used for the purpose of description.

Various references are cited throughout this specification, each of which is incorporated herein by reference in its entirety.

What is claimed is:

1. A method for identifying an individual who may be susceptible to alcoholism or to the pathological effects of alcohol consumption comprising detecting the presence or absence of a mutation that leads to a pseudodeficiency (PD) phenotype in each allele of an arylsulfatase A (ASA) gene of an individual, and identifying whether the individual is homozygous, heterozygous, or normal for the PD mutation of the ASA gene, wherein homozygosity for the PD mutation of the ASA gene indicates that the individual may be susceptible to alcoholism or to the pathological effects of alcohol consumption.

2. The method according to claim 1, wherein the method of identifying whether an individual is homozygous, heterozygous or normal for a PD mutation comprises detecting a mutation in a residue 350 N-glycosylation site of ASA or by detection of a mutation of nucleotide corresponding to nucleotide 1049 of ASA cDNA, wherein homozygosity for the PD mutation of the ASA gene indicates that the individual may be susceptible to alcoholism or to the pathological effects of alcohol consumption.

3. The method according to claim 2, wherein the mutation is detected by analyzing polymerase chain reaction (PCR) amplified genomic DNA or mRNA, wherein the PCR product of the mutant and normal N-glycosylation site can be differentiated by specific restriction endonucleases.

4. The method according to claim 3, wherein the PCR analysis is performed by:
 a) amplifying an approximately 200-base pair segment of genomic DNA with a 5' primer TGATGGCGAACT-GAGTGACT (SEQ ID NO:9) and a 3' primer AAG-GATCTGGGATCAGGGGT (SEQ ID NO:10); and
 b) detecting the presence of a BsrI restriction endonuclease site;
wherein the BsrI endonuclease site is present in the PD mutant ASA allele.

5. The method according to claim 3, wherein the PCR analysis is performed on DNA obtained from buccal cells.

6. The method according to claim 2, wherein the mutation is detected by analyzing polymerase chain reaction (PCR) amplified genomic DNA or mRNA and detecting hybridization of an oligonucleotide probe specific for a mutant or native ASA gene at position corresponding to nucleotide 1049 of the cDNA.

7. The method according to claim 6, wherein the hybridization analysis comprises hybridization of an oligonucleotide probe selected from the group consisting of AAGGT-GACATTGGGCAGTGG (SEQ ID NO:5) and AAGGTGACACTGGGCAGTGG (SEQ ID NO:6) to the amplified sequence, wherein hybridization of the former probe at 55° C. with washing at 62° C. is indicative of a normal ASA allele, and hybridization of the latter probe at 55° C. with washing at 60° C. is indicative of a PD allele.

8. The method according to claim 6, wherein the PCR analysis is performed on DNA obtained from buccal cells.

9. The method according to claim 2, wherein the mutation is detected by analyzing genomic DNA by Southern hybridization analysis with an oligonucleotide probe specific for a mutant or native ASA gene at position corresponding to nucleotide 1049 of the cDNA.

10. The method according to claim 9, wherein the hybridization analysis comprises hybridization of an oligonucleotide probe selected from the group consisting of AAGGT-GACATTGGGCAGTGG (SEQ ID NO:5) and AAGGTGACACTGGGCAGTGG (SEQ ID NO:6) to the genomic DNA, wherein hybridization of the former probe at 55° C. with washing at 62° C. is indicative of a normal ASA allele, and hybridization of the latter probe at 55° C. with washing at 60° C. is indicative of a PD allele.

11. The method according to claim 2, wherein the mutation is detected by sequencing both alleles.

12. The method according to claim 2, wherein the mutation is detected by detecting a difference in the relative electrophoretic mobility of an ASA protein from an individual possessing the mutant ASA enzyme as compared to a normal ASA protein, which is indicative of a mutation in the residue 350 N-glycosylation site.

13. The method according to claim 12, wherein the PD mutant ASA has an apparent molecular weight of about 59 kD by PAGE, and normal ASA has an apparent molecular weight of about 62 kD by PAGE.

14. The method according to claim 12, comprising detecting a mobility difference after endo-N-acetylglucosaminidase H (endo-H) treatment of the ASA, wherein mutant ASA has a smaller loss of mass after endo-H treatment than normal ASA.

15. The method according to claim 2, wherein the mutation is detected by detecting the absence of an N-linked glycan moiety of an ASA protein compared to a normal ASA protein, which is indicative of a mutation in the residue 350 N-glycosylation site.

16. The method according to claim 2, wherein the mutation is detected by comparing amount of binding of an antibody specific for an epitope containing residue 350 of ASA lacking a residue 350 N-glycosylation site, wherein the antibody does not bind to normal ASA, with an amount of binding of an antibody that binds to all forms of ASA, wherein
 a) if the amount of ASA bound by the antibody specific for mutant ASA is about the same as the amount bound by the antibody reactive with all ASA, then the individual is homozygous for the PD alleles;
 b) if the amount of ASA bound by the antibody specific for mutant ASA is about the half the amount bound by the antibody reactive with all ASA, then the individual is heterozygous for the PD alleles; and
 c) if the amount of ASA bound by the antibody specific for mutant ASA is undetectable, then the individual is homozygous normal.

17. The method according to claim 16, wherein the antibody specific for an epitope containing residue 350 of ASA lacking an N-glycosylation site is generated against the peptide Ac-CAPLPSVTDGFD-NH$_2$ (SEQ ID NO:13).

18. The method according to claim 2, wherein the mutation is detected by determining a reduction of ASA enzymatic activity to 10–30% of normal.

19. The method according to claim 2, wherein the mutation comprises substitution of guanine for adenine at nucleotide position 1049 of cDNA for ASA.

20. The method according to claim 2, further comprising detecting a mutation in the in the polyadenylation signal sequence of the allele of ASA.

21. The method according to claim 1, wherein the method of identifying whether an individual is homozygous heterozygous, or normal for a PD mutation comprises detecting a mutation in the residue 350 N-glycosylation site of ASA and detecting a mutation in the polyadenylation signal sequence of the allele of ASA.

22. The method according to claim 21, wherein the mutation in the polyadenylation signal sequence is detected by analyzing polymerase chain reaction (PCR) amplified genomic DNA or mRNA, wherein the PCR product of the mutant and normal polyadenylation signal sequence can be differentiated by specific restriction endonucleases.

23. The method according to claim 22, wherein the PCR analysis is performed by:
 a) amplifying about an approximately 182-base pair segment of genomic DNA with a 5' primer AGCTTGCT-GCCATTGCCCA (SEQ ID NO:11) and a 3' primer CATTACCCCAGGATTGGTCGAA (SEQ ID NO:12); and
 b) detecting the presence of two MaeIII restriction endonuclease sites;
wherein two MaeIII endonuclease sites are present in the PD mutant ASA allele.

24. The method according to claim 22, wherein the PCR analysis is performed on DNA obtained from buccal cells.

25. The method according to claim 21, wherein the mutation in the polyadenylation signal sequence is detected by analyzing polymerase chain reaction (PCR) amplified genomic DNA or mRNA and detecting hybridization under high stringency conditions of an oligonucleotide probe specific for a mutant or native ASA gene at position corresponding to nucleotide 1620 of the cDNA.

26. The method according to claim 25, wherein hybridization analysis comprises hybridization of an oligonucleotide probe selected from the group consisting of CTGGT-GTTATTACGTTATC (SEQ ID NO:7) and CTGGTGTTACTACGTTATC (SEQ ID NO:8) to the amplified sequence, wherein hybridization of the former probe at 48° C. with washing at 52° C. is indicative of a normal ASA allele, and hybridization of the latter probe at 48° C. with washing at 52° C. is indicative of a PD allele.

27. The method according to claim 25, wherein the PCR analysis is performed on DNA obtained from buccal cells.

28. The method according to claim 21, wherein the mutation in the polyadenylation signal sequence is detected by analyzing genomic DNA by Southern hybridization analysis with an oligonucleotide probe specific for a mutant or native ASA gene at position corresponding to nucleotide 1620 of the cDNA.

29. The method according to claim 28, wherein hybridization analysis comprises hybridization of an oligonucleotide probe selected from the group consisting of CTGGTGTTATTACGTTATC (SEQ ID NO:7) and CTGGTGTTACTACGTTATC (SEQ ID NO:8) to the genomic DNA, wherein hybridization of the former probe at 48° C. with washing at 52° C. is indicative of a normal ASA allele, and hybridization of the latter probe at 48° C. with washing at 52° C. is indicative of a PD allele.

30. The method according to claim 21, wherein the presence or absence of the mutation in the polyadenylation signal sequence is detected by sequencing both ASA alleles.

31. The method according to claim 22, wherein the mutation comprises substitution of guanine for adenine at nucleotide position 1620 of cDNA for ASA.

32. An antibody specific for an epitope containing residue 350 of ASA lacking an N-glycosylation site, wherein the antibody does not bind to normal ASA containing the N-glycosylation site.

33. The antibody of claim 32, which antibody is a monoclonal antibody.

34. The antibody of claim 32, wherein the antibody is generated against the peptide Ac-CAPLPSVTDGFD-NH₂ (SEQ ID NO:13).

35. A kit for identifying an individual who is susceptible to alcoholism comprising:

a) the antibody specific for an epitope containing residue 350 of ASA lacking the N-glycosylation site of claim 32;

b) an antibody specific for all forms of ASA; and c) means for quantitating binding of the antibody specific for an epitope and the antibody specific for all forms of ASA to ASA in a sample from an individual.

36. A kit for identifying an individual who is susceptible to alcoholism comprising:

a) a 5' primer having the sequence TGATGGCGAACTGAGTGACT (SEQ ID NO:9) and a 3' primer having the sequence AAGGATCTGGGATCAGGGGT (SEQ ID NO:10);

b) an BsrI restriction endonuclease;

c) a 5' primer having the sequence AGCTTGCTGCCATTGCCCA (SEQ ID NO:11) and a 3' primer having the sequence CATTACCCCAGGATTGGTCGAA (SEQ ID NO:12); and d) a MaeIII restriction endonuclease.

37. A kit for identifying an individual who is susceptible to alcoholism comprising:

a) a 5' primer having the sequence TGATGGCGAACTGAGTGACT (SEQ ID NO:9) and a 3' primer having the sequence AAGGATCTGGGATCAGGGGT (SEQ ID NO:10); and b) an BsrI restriction endonuclease.

38. A kit for identifying an individual who is susceptible to alcoholism comprising:

a) a 5' primer having the sequence AGCTTGCTGCCATTGCCCA (SEQ ID NO:11) and a 3' primer having the sequence CATTACCCCAGGATTGGTCGAA (SEQ ID NO:12); and b) a MaeIII restriction endonuclease.

39. An oligonucleotide selected from the group consisting of

TGATGGCGAACTGAGTGACT (SEQ ID NO:9); AAGGATCTGGGATCAGGGGT (SEQ ID NO:10); AGCTTGCTGCCATTGCCCA (SEQ ID NO:11); and CATTACCCCAGGATTGGTCGAA (SEQ ID NO:12).

40. A method for identifying an individual carrying a pseudodeficiency (PD) mutation of an allele of an arylsulfatase A (ASA) gene, comprising detecting a mutation at nucleotide position 1049 of the cDNA of least one allele of ASA by polymerase chain amplification (PCR) analysis, wherein the PCR product of the mutant and normal allele can be differentiated by specific restriction endonucleases.

41. The method according to claim 40, wherein the PCR analysis is performed by:

a) amplifying an approximately 200-base pair segment of genomic DNA with a 5' primer TGATGGCGAACTGAGTGACT (SEQ ID NO:9) and a 3' primer AAGGATCTGGGATCAGGGGT (SEQ ID NO:10); and b) detecting the presence of a BsrI restriction endonuclease site;

wherein the BsrI endonuclease site is present in the PD mutant ASA allele.

42. A method for identifying an individual carrying a pseudodeficiency (PD) mutation of an allele of an arylsulfatase A (ASA) gene, comprising detecting a mutation in a polyadenylation signal sequence corresponding to nucleotide position 1620 of the cDNA of at least one allele of ASA by polymerase chain amplification (PCR) analysis, wherein the PCR product of the mutant and normal polyadenylation signal sequence can be differentiated by specific restriction endonucleases.

43. The method according to claim 42, wherein the PCR analysis is performed by:

a) amplifying about an approximately 182-base pair segment of genomic DNA with a 5' primer AGCTTGCTGCCATTGCCCA (SEQ ID NO:11) and a 3' primer CATTACCCCAGGATTGGTCGAA (SEQ ID NO:12); and b) detecting the presence of two MaeIII restriction endonuclease sites;

wherein two MaeIII endonuclease sites are present in the PD mutant ASA allele.

44. A method for identifying an individual carrying a pseudodeficiency (PD) mutation of an allele of an arylsulfatase A (ASA) gene, comprising a) detecting a mutation in a residue 350 N-glycosylation site of at least one allele of ASA by polymerase chain amplification (PCR) analysis, wherein the PCR product of the mutant and normal N-glycosylation site can be differentiated by specific restriction endonucleases; and b) detecting a mutation in a polyadenylation signal sequence of at least one allele of ASA by polymerase chain amplification (PCR) analysis, wherein the PCR product of the mutant and normal polyadenylation signal sequence can be differentiated by specific restriction endonucleases.

* * * * *